US012564389B2

(12) United States Patent
Shalon

(10) Patent No.: US 12,564,389 B2
(45) Date of Patent: Mar. 3, 2026

(54) DEVICES AND METHODS FOR SAMPLING GASTROINTESTINAL FLUIDS AND ASSESSING GASTROINTESTINAL FUNCTION

(71) Applicant: Envivo Bio Inc., San Carlos, CA (US)

(72) Inventor: Tidhar Dari Shalon, Los Altos Hills, CA (US)

(73) Assignee: Envivo Bio Inc, San Carlos, CA (US)

( * ) Notice: Subject to any disclaimer, the term of this patent is extended or adjusted under 35 U.S.C. 154(b) by 389 days.

(21) Appl. No.: 18/253,938

(22) PCT Filed: Nov. 22, 2021

(86) PCT No.: PCT/US2021/060402

§ 371 (c)(1),
(2) Date: May 23, 2023

(87) PCT Pub. No.: WO2022/109425

PCT Pub. Date: May 27, 2022

(65) Prior Publication Data

US 2024/0008858 A1 Jan. 11, 2024

Related U.S. Application Data

(60) Provisional application No. 63/117,409, filed on Nov. 23, 2020.

(51) Int. Cl.
*A61B 10/00* (2006.01)
*B01L 3/00* (2006.01)

(52) U.S. Cl.
CPC ...... *A61B 10/0045* (2013.01); *B01L 3/50273* (2013.01); *B01L 3/5085* (2013.01); *A61B 2010/0061* (2013.01)

(58) Field of Classification Search
CPC ........ A61B 10/0045; A61B 2010/0061; B01L 3/50273; B01L 3/5085
USPC .......................................................... 600/581
See application file for complete search history.

(56) References Cited

U.S. PATENT DOCUMENTS

| | | | |
|---|---|---|---|
| 2,508,690 A | 5/1950 | Schmerl | |
| 2,907,326 A | 10/1959 | Horace | |
| 3,066,672 A | 12/1962 | Crosby, Jr. et al. | |
| 3,315,660 A | 4/1967 | Abella | |
| 3,485,235 A | 12/1969 | Felson | |
| 3,528,429 A | 9/1970 | Beal et al. | |
| 3,683,890 A * | 8/1972 | Beal ...................... | A61B 10/02 600/431 |

(Continued)

FOREIGN PATENT DOCUMENTS

| | | | |
|---|---|---|---|
| CN | 105050500 A | 11/2015 | |
| CN | 212346576 U * | 1/2021 | |

(Continued)

OTHER PUBLICATIONS

International Search Report and Written Opinion issued in PCT Application No. PCT/US2021/060402, mailed Mar. 17, 2022, in 9 pages.

*Primary Examiner* — Mark Edwards
(74) *Attorney, Agent, or Firm* — Knobbe, Martens, Olson & Bear, LLP

(57) ABSTRACT

Embodiments of devices and methods for sampling gastro-intestinal fluids and assessing gastrointestinal function using a device comprising a sampling tube are provided.

15 Claims, 7 Drawing Sheets

(56) References Cited

U.S. PATENT DOCUMENTS

| | | | |
|---|---|---|---|
| 4,186,730 | A | 2/1980 | Bucalo |
| 4,187,860 | A | 2/1980 | Villari |
| 4,481,952 | A | 11/1984 | Pawelec |
| 4,643,192 | A | 2/1987 | Fiddian-Green |
| 4,685,472 | A | 8/1987 | Muto |
| 4,735,214 | A | 4/1988 | Berman |
| 5,479,923 | A | 1/1996 | Rantala |
| 5,611,787 | A | 3/1997 | Demeter et al. |
| 5,738,110 | A | 4/1998 | Beal et al. |
| 5,971,942 | A | 10/1999 | Gu et al. |
| 6,149,607 | A | 11/2000 | Simpson et al. |
| 7,037,275 | B1 | 5/2006 | Marshall et al. |
| 11,766,249 | B2 | 9/2023 | Shalon |
| 12,096,920 | B1 | 9/2024 | Shalon |
| 12,349,873 | B2 | 7/2025 | Shalon |
| 2004/0039350 | A1 | 2/2004 | McKittrick |
| 2004/0097834 | A1 | 5/2004 | Stoltz |
| 2007/0161928 | A1 | 7/2007 | Sprenkels et al. |
| 2007/0173738 | A1 | 7/2007 | Stoltz |
| 2008/0208077 | A1 | 8/2008 | Iddan et al. |
| 2009/0216082 | A1 | 8/2009 | Rabinovitz |
| 2009/0216085 | A1 | 8/2009 | Yamazaki |
| 2011/0060189 | A1 | 3/2011 | Belson |
| 2011/0208011 | A1 | 8/2011 | Ben-Horin |
| 2014/0303461 | A1 | 10/2014 | Callaghan et al. |
| 2015/0064241 | A1 | 3/2015 | Conrad |
| 2016/0038086 | A1 | 2/2016 | Wrigglesworth et al. |
| 2017/0296092 | A1 | 10/2017 | Jones et al. |
| 2018/0164221 | A1 | 6/2018 | Singh et al. |
| 2019/0287657 | A1 | 9/2019 | Holmes et al. |
| 2020/0138416 | A1 * | 5/2020 | Shalon .............. A61B 10/0045 |
| 2020/0146541 | A1 | 5/2020 | Yangdai et al. |
| 2020/0323422 | A1 | 10/2020 | Duan |
| 2022/0175351 | A1 | 6/2022 | Shalon |
| 2023/0389902 | A1 | 12/2023 | Shalon |
| 2024/0398394 | A1 | 12/2024 | Shalon |

FOREIGN PATENT DOCUMENTS

| | | | |
|---|---|---|---|
| JP | S-5376584 | 7/1978 | |
| JP | H05-228128 | 9/1993 | |
| WO | WO 79/00811 | 10/1979 | |
| WO | WO 88/09162 | 12/1988 | |
| WO | WO 2005/046485 | 5/2005 | |
| WO | WO 2013/120184 | 8/2013 | |
| WO | WO 2014/140334 | 9/2014 | |
| WO | WO 2017/211872 A1 | 12/2017 | |
| WO | WO 2018/183941 A2 | 10/2018 | |
| WO | WO 2018/213729 A1 | 11/2018 | |
| WO | WO-2020185326 A1 * | 9/2020 | .......... C12Q 1/6886 |
| WO | WO 2022/109425 A1 | 5/2022 | |

* cited by examiner

Glycocholic acid across time

DEVICES AND METHODS FOR SAMPLING GASTROINTESTINAL FLUIDS AND ASSESSING GASTROINTESTINAL FUNCTION

CROSS REFERENCE TO RELATED APPLICATIONS

This application is a national stage application of the Patent Cooperation Treaty (PCT) international application titled "Devices And Methods For Sampling Gastrointestinal Fluids And Assessing Gastrointestinal Function", international application number PCT/US2021/60402, filed in the United States Patent And Trademark Office on Nov. 22, 2021, which claims priority to and the benefit of the provisional patent application titled "Devices and Methods for Sampling Gastrointestinal Fluids and Assessing Gastrointestinal Function", application No. 63/117,409, filed in the United States Patent and Trademark Office on 23 Nov. 2020. The specifications of the above referenced patent applications are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of gastrointestinal diagnosis and treatment.

BACKGROUND

It has recently been recognized that the mammalian gastrointestinal (GI) tract plays a central role in health and disease. In addition, the gastrointestinal microbiomes perform many vital physiological functions that benefit their host organism, comprising digestion, producing essential amino acids and vitamins, regulating the immune system, providing resistance to disease, and even modifying appetite, and behavior. Yet we know very little about the functions of hundreds or thousands of microbial species and their associated primary and secondary metabolites in mammalian GI tracts. The variety of microbes in a single individual at different points of the GI tract is staggering. Due to the complexity of this microbial ecology in a single individual and the variability among individuals, there exists a need to routinely sample and analyze the luminal contents and the microbial community living in all regions of the GI tract, along with their associated metabolites, as well as their interactions with the host. Microbial secondary metabolites play a key role in the two-way communication between microbes and their hosts and can greatly impact the physiological state of the host. The analyses of the gut metabolism and gut microbes can correlate to states of health and disease, as well as guide and measure the effect of treatment.

There is therefore a need to sample gastrointestinal fluids in a safe and non-invasive manner on a routine basis for analysis of the biochemical, immunological, metabolic and microbial processes occurring therein. Ideally, samples will be recovered and stored in the collection device in the same aerobic or anaerobic state of their natural intestinal surroundings. Given the diversity of functions and biochemical environments present in the GI tract, the collected samples should be as representative of the entire GI tract as possible, rather than simply sampling a few regions. It is important to quantify the physical and temporal gradients of the parameters being measured, as opposed to just measuring the absolute levels of the parameters. Furthermore, collected samples should not be contaminated with adjacent luminal contents due to the exponential increase in microbial content along the GI tract and the very different processes occurring in the different regions of the GI tract. The above points imply that the sampling of the GI tract should be continuous, or performed at regular intervals, during the transit of the device through the GI tract. The above points further imply that the samples should be separated from each other either with sufficient physical distance in a linear array or with mechanical barriers in order to prevent cross contamination between the samples. Lastly, sampling must be done using a device and methods that are safe and do not cause discomfort for the subject in order for GI sampling to become a routine part of medical practice.

SUMMARY OF THE DISCLOSURE

The present invention relates to devices and methods for collecting gastrointestinal samples using a device comprising a portion that is swallowed. Also disclosed are methods of assessing gastrointestinal function following ingestion of a stimulus agent. Stimulus agents comprise ingestion of dietary elements, microbes, prebiotics, active agents such as drugs, xenobiotics, or combinations thereof. Ingestion can be orally or through a dispensing tube that is also part of the device. Alternatively, the sampling and dispensing tube can be the same tube with flow going out of the body and into the body respectively, through the same tube, with an optional rinse step in between. Administration of a stimulus agent is coupled and coordinated with the collection of gastrointestinal samples using the sampling device. The stimulus agent is then correlated with the physiological, immunological, metabolic and/or microbial processes occurring in the GI tract as evidenced by an analysis of the collected gastrointestinal samples. Gastrointestinal samples can include the unaltered or altered stimulus agent, along with the microbes that acted on the stimulus agent and the surrounding biochemical milieu that can be used to determine the region of the GI tract in which the stimulus agent occurred.

In an initial aspect, a device for collecting gastrointestinal samples is provided. The device comprises a sampling tube that collects samples throughout the GI tract. The sampling tube comprises a distal end that travels in the GI tract, and a proximal end that stays outside the subject's body while the device is active. The proximal end of the sampling tube is connected to a reservoir. The reservoir, which can be in the form of a tube, sits inside an external enclosure that also comprises the portion of the sampling tube that has not yet been swallowed. The distal portion of the sampling tube comprises an inlet portion with one or more holes that allows gastrointestinal samples to enter the sampling tube.

In an additional aspect, the external enclosure is mounted on the head or around the neck of the of the user.

In an additional aspect, the distal portion of the sampling tube is connected to a head element that increases the peristalsis force acting on the sampling tube pulling it through the GI tract.

In an additional aspect, a string or a portion of the sampling tube of sufficient length to allow the head element to enter the esophagus is packed inside, wound inside or wound outside the head element.

In one aspect, at least a portion of the sampling tube is wound inside or outside the head element or in a separate capsule connected to the head element.

In a further aspect, the sampling tube is elastically collapsed in the radial direction when wound inside or outside the head element to eliminate the internal lumen space.

In an additional aspect, a head element and/or a string or portion of the sampling tube are both packed into a water-soluble or enterically coated capsule.

In an additional aspect, the head element is compressed inside a water-soluble capsule and the head element inflates or expands once the head element is in the GI tract.

In an additional aspect, the inlet portion of the sampling tube is sealed until the inlet portion arrives at the initial location to sample in the GI tract.

In an additional aspect, a gas or fluid is perfused through the sampling tube from the proximal end to the distal end and through the inlet portion until the inlet portion arrives at the initial location to sample in the GI tract.

In an additional aspect, a control unit in the device controls the timing and rate of flow of fluids and/or gases through the sampling and/or dispensing tubes.

In an additional aspect, at least a portion of the sampling tube is packed or wound in an external enclosure kept outside the body of the subject. The portion of the sampling tube that is not introduced into the GI tract is kept in the external enclosure.

In an additional aspect, the rate of the sampling tube that is allowed outside the external enclosure is controlled by an actuator and/or a control unit.

In an additional aspect, the length and dwell time of the sampling tube that is allowed outside the external enclosure is pre-programmed by a health care professional via a control unit so that a specific region of the GI tract is sampled and/or stimulated.

In a further aspect, the device releases electrical stimuli to the GI tract in order to accelerate peristalsis, thereby shortening the duration of the procedure.

In a further aspect, the device releases prokinetic agents to the GI tract in order to accelerate peristalsis, thereby shortening the duration of the procedure.

In an additional aspect, the outer diameter of the sampling tube is 2.5 mm or smaller, preferably 2 mm or smaller and most preferably 1 mm or smaller. This diameter tube is much smaller than the 3 mm and greater outer diameter of prior art feeding tubes.

In an additional aspect, detecting means measure one or more physical, chemical or biological parameters of the sampled fluids and/or the environment in the region of the head element and feed this information to the control unit.

In an additional aspect, gastrointestinal samples are extracted based on the levels of one or more sampling parameters.

In an additional aspect, gastrointestinal samples move from the sampling tube into a reservoir tube outside the subject's body and are stored in a linear array.

In an additional aspect, a separating agent is introduced into the sampling and/or reservoir tube at time intervals to create a diffusion barrier of microbes or analytes along the sampling and/or reservoir tube.

In an additional aspect, the samples arriving through the sampling tube are diverted into discrete collection chambers, thereby separating the collected GI fluids in discrete sample containers.

In an additional aspect, a preserving agent is introduced into the collected GI samples inside the device.

In an additional aspect, the reservoir tube is an extension of the sampling tube.

In an additional aspect, the linear array of gastrointestinal samples stored in the reservoir tube is a recapitulation of the linear order of the fluids collected from the GI tract.

In an additional aspect, an evacuated chamber provides the vacuum force that drives samples into the sampling tube.

In an additional aspect, a direct displacement vacuum pump provides the vacuum force that drives samples into the sampling tube.

In an additional aspect, the actuation of one of more valves controls the flow of samples into the sampling tube.

In an additional aspect, the flow of gastrointestinal samples into the sampling tube is driven by a pump.

In an additional aspect, the head element comprises a pump that forces GI fluids through the sampling tube and out of the body using positive pressure or direct displacement.

In an additional aspect, power to the pump in the head element is stored in batteries inside the head element.

In an additional aspect, power to the pump is transferred from outside the body using conductive elements that run alongside or inside the sampling tube.

In an additional aspect, a tube connects a pressure source outside the body to an inflatable bladder in a pump chamber inside the head element. Deflation of the bladder forces fluids from the GI tract through a one-way valve into the pump chamber. Inflation of the bladder forces fluids from the pump chamber through a one-way valve through the sampling tube and into a collection chamber.

In a further aspect, the head element comprises two nested balloons, an inner and outer balloon that function as a pump to transfer gastrointestinal fluids via the sampling tube and into the collection chamber by utilizing two one-way valves in the outer balloon.

In a further aspect, a tube connects a pressure source outside the body to a piston elastically-biased to pull fluids from the GI tract through a one-way vale into a pump chamber.

In an additional aspect, the flow of gastrointestinal samples into the sampling tube occurs in an oscillatory manner.

In an additional aspect, the flow of gastrointestinal samples into the sampling tube is automatically reversed for a brief period to clear a blockage as soon as lack of adequate forward flow of gastrointestinal samples inside sampling tube is detected by a flow sensor.

In an additional aspect, the inlet portion of the sampling tube is surrounded by a filtering element with a pore size smaller than the inner diameter of the sampling tube.

In an additional aspect, the inlet portion of the sampling tube is surrounded by a cage that prevents the mucosal surface of the GI tract from collapsing on the inlet portion of the sampling tube and blocking flow therein.

In an additional aspect that increases the surface area of the filtering element, at least a portion of the head element and the inlet portion of the sampling tube are surrounded by a filtering element with a pore size smaller than the inner diameter of the sampling tube.

In an additional aspect, the dead volume between the filtering element and the inlet portion of the sampling tube is 250 microliters or less.

In an additional aspect, the macroscopic surface area of the filtering element when laid out as a flat sheet is at least 0.25 square centimeters.

In an additional aspect, the filtering element covers at least a portion of the circumferential surface of a capsule-shaped head element.

In an additional aspect, the inlet portion of the sampling tube is placed at the circumferential surface of the head element.

In an additional aspect, the inlet portion of the sampling tube is elastically biased radially outward from the head element to push against the mucosal surface of the GI tract.

In an additional aspect, the head element mechanically degrades after being present in the GI tract for a predetermined time range.

In an additional aspect, the head element is connected to the sampling tube by a connector, adhesive or electrically activated fuse element.

In a further aspect, the head element is inflatable and detaches from the sampling tube at a certain minimum pressure of inflation of the head element.

In an additional aspect, the head element comprises a swelling polymer that grows in size when exposed to the moisture of the GI tract.

In an additional aspect, the sampling tube emerges from the external enclosure as the sampling tube is pulled further into the GI tract.

In an additional aspect, the distance traveled by the inlet portion of the sampling tube in the GI tract is computed in the control unit by measuring the length of sampling tube that emerges from the external enclosure.

In an additional aspect, detecting means outside the subject's body or in a portion of the device within the subject's body measure a parameter of the gastrointestinal fluids in real time as they flow into the reservoir tube and this information is transferred to a control unit.

In an additional aspect, a linear map of analytes of interest along the GI tract is created by correlating the concentrations of the analytes of interest that were collected along the GI tract with the inferred location of the inlet portion of the device in the GI tract at the time the analytes were collected. Example analytes comprise the genetic identity of microbes, inflammatory markers and blood.

In an additional aspect, detachment of the head element from the sampling tube or deflation of the head element is initiated by the control unit.

In an additional aspect, the sampling tube, which is up to 5 meters long, comprises shorter sections that are connected with linker elements that mechanically degrade in moisture over a preset time period.

In an additional aspect, the sampling tube has radial protrusions at linear intervals to assist in advancing the sampling tube through the GI tract via peristalsis.

In an additional aspect, gastrointestinal fluids are collected and analyzed in order to measure the response in the GI tract to a stimulus agent.

In an additional aspect, the amount of ingested stimulus agent and the timing of ingestion are coordinated so that the ingested stimulus agent arrives at the region of interest of the GI tract at the same time that the device is collecting samples in the region of interest.

In an additional aspect, the device comprises one or more stimulus agents in storage compartments that are introduced into the GI tract via the sampling tube or a separate dispensing tube.

In another aspect, a method of optimizing drug selection, formulation, release profile, or dose comprises dosing a subject with one or more candidate drugs, collecting gastrointestinal samples before and after drug administration, and determining the favorable drug parameters based on analyzing the collected gastrointestinal samples that have been altered by the drug or that include the drug at varying stages of metabolism. Example analyses comprise presence or absence of specific drug metabolites, host or microbial drug metabolism or transformation, presences of microbes or their genes or protein products, and changes to host physiology including host molecules created, modified or depleted in response to the drug.

In another aspect, the device measures a parameter of interest throughout the GI tract and the control unit releases an active agent when such a parameter is detected at an appropriate level.

In another aspect, the device collects gastrointestinal samples through the sampling tube and also delivers active agents through the same sampling tube by reversing the direction of the flow of fluids though the sampling tube.

In a further aspect, a microbe, enzyme, metabolite, peptide, small molecule, and/or prebiotic can be delivered to a region of the GI tract through the sampling tube, and then after a time delay, GI luminal contents can be collected via the same sampling tube to determine the response of the host or gut microbiota to the stimulating microbe, enzyme, metabolite, peptide, small molecule, and/or prebiotic.

In a further aspect, the duration of the GI tract response to a stimulus agent is measured optically.

In a further aspect, the control unit of the device will notify or prompt the subject at the optimal time to ingest a dietary stimulus agent based on the inferred location and calculated velocity of the inlet portion of the sampling tube in the GI tract, and the predicted time required for the dietary stimulus agent to transit the GI tract.

In an additional aspect, the sampling tube and head element are swallowed by the user after a fast of at least 8 hours and within 2 hours of the consumption of a test meal of 250 calories or less, or preferably 150 calories or less.

In a further aspect, a device for collecting gastrointestinal samples comprises a sampling tube in fluid communication with a collection chamber, wherein the collection chamber is positionable outside a subject's body when the sampling tube is within the gastrointestinal tract of the subject.

In a further aspect, the collection chamber is a reservoir tube in which the collected gastrointestinal samples are stored as a linear array.

In a further aspect, the linear array of collected gastrointestinal samples inside the reservoir tube are interspersed with bubbles of a non-miscible fluid or gas.

In a further aspect, a pressure differential between the collection chamber and the gastrointestinal tract moves the gastrointestinal samples from the sampling tube into the collection chamber.

In a further aspect, a method of assessing the influence of a stimulus agent on the gastrointestinal tract of a subject comprises:

(a) introducing a sampling tube into the gastrointestinal tract of a subject and allowing the sampling tube to advance through the gastrointestinal tract under normal peristaltic forces;

(b) collecting a first sample into the sampling tube;

(c) introducing a stimulus agent to the subject;

(d) collecting a second sample into the sampling tube, and (e) analyzing a difference between the first and the second samples thereby assessing the influence of a stimulus agent on the gastrointestinal tract of a subject.

In a further aspect, a method of dispensing a compound into the gastrointestinal tract and collecting a gastrointestinal sample comprises:

(a) introducing one or more tubes into the gastrointestinal tract of a subject and allowing the one or more tubes to advance through the gastrointestinal tract;

(b) administering a compound through the one or more tubes; and (c) collecting gastrointestinal fluids into the one or more tubes.

In a further aspect, the one or more tubes include a dispensing tube and a sampling tube.

In a further aspect, the one or more tubes include a single tube for dispensing and sampling.

In a further aspect, a device for collecting gastrointestinal samples from a subject comprises a sampling tube and a head element, wherein at least a portion of the sampling tube is compressed or wound on the inside or outside of the head element.

In a further aspect, the volume of collected gastrointestinal samples is at least 100 microliters of fluid, preferably at least 250 and more preferably at least 1 milliliter of fluid.

In a further aspect, the sampling tube is unwound or uncompressed from inside or outside of a head element as the head element is advanced through the gastrointestinal tract via normal peristalsis.

In a further aspect, a device for collecting gastrointestinal samples from a subject comprises a sampling tube with proximal and distal ends and a pump positioned towards the distal end of the sampling tube.

In a further aspect, the pump comprises an inflatable bladder or displaceable piston inflated or displaced by pressure delivered from outside the subject.

In a further aspect, a capsule device is configured for delivering a stimulus agent to a region of a gastrointestinal tract and for collecting gastrointestinal fluids from the same region.

In a further aspect, a method of assessing the influence of a stimulus agent on the gastrointestinal tract of a subject comprises administering the capsule device above into the gastrointestinal tract of a subject.

In a further aspect, the device comprises an untethered capsule that captures the response of the GI tract to a stimulus agent in the region of interest.

In a further aspect, a plurality of untethered device capsules is ingested at one time or at known time intervals, wherein each capsule device is designed to sample a different region of the GI tract.

In a further aspect, an untethered capsule-shaped device comprises both a stimulus agent and a collecting chamber.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
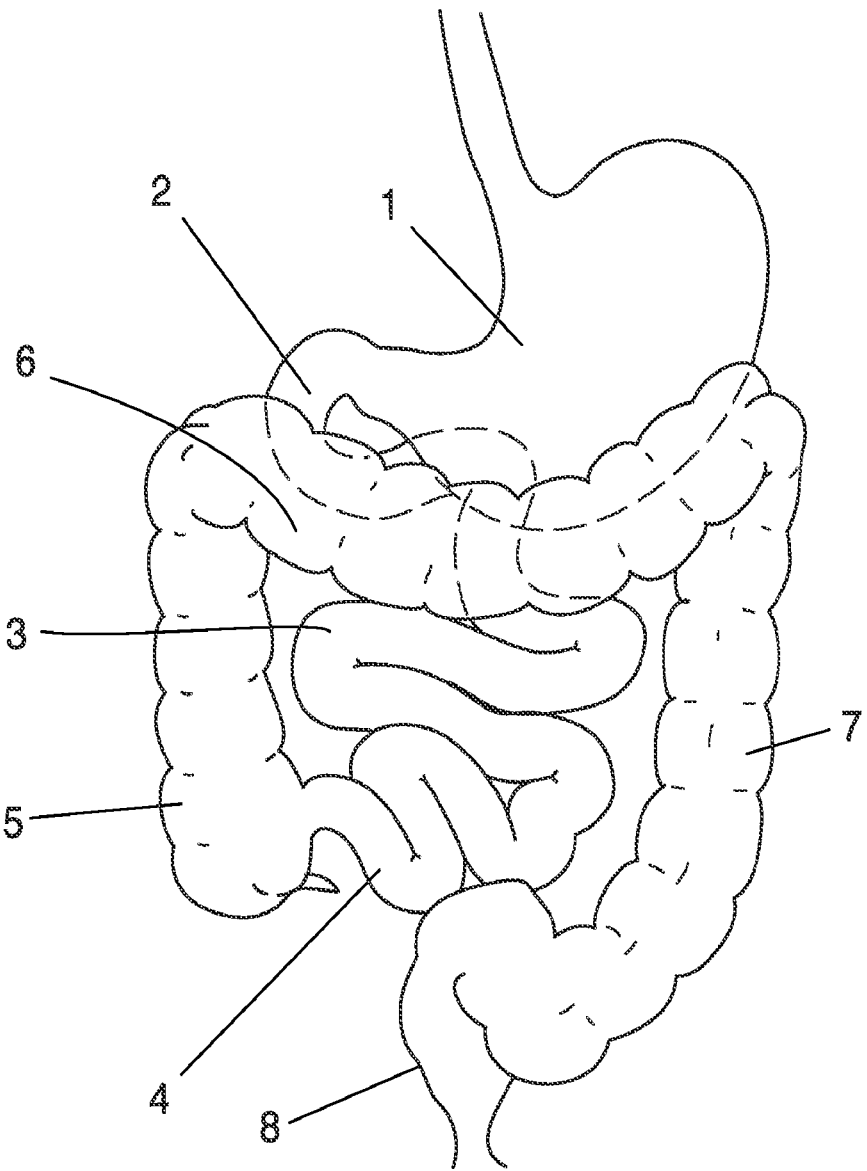
FIG. 1 illustrates the anatomy of the human gastrointestinal tract.

As used herein, the terms "gastrointestinal samples" or "analytes" comprise fluids, liquids, digestive juices, bile acids, mucus, mucins, microbes, metabolites, cells, cell fragments, carbohydrates, fats, lipids, proteins, peptides, immune system molecules, immune system cells, epithelial cells, blood, hemoglobin, food particles, acids, bases, gases, small molecules, hormones, nucleic acids, drugs, pro-drugs, drug metabolites, volatile molecules, dissolved or free gases, and other molecules present in the GI tract from the mouth to the anus that are analyzed using any number of analytical techniques known in the art.

As used herein, "gastrointestinal fluids" comprise the luminal contents of the gastrointestinal tract that are monitored according to one or more sampling parameters. Depending on the sampling parameters, subsets of gastrointestinal fluids are collected as gastrointestinal samples for further analysis.

As used herein, "sampling parameters" comprise pH, color, dissolved oxygen, reduction/oxidation potential, gas content, presence of lipids, spectrophotometer characteristics, spectrometry characteristics, biochemical content, microbial content, metabolic content, immunological content, location in the GI tract of the inlet portion of sampling tube, and elapsed time since a previous event.

As used herein, the term "microbe" comprises one or more species or strains of microscopic agents from the three domains eubacteria, eukarya and archaea as well as viruses such as phages. As used herein, a group of microbes, or a microbial population, taken as a whole is referred to as a "microbiota" and when the group is quantitated or measured in some manner it is referred to as a "microbiome."

As used herein, the terms "immune system molecules or immune system cells" comprise all forms of lymphocytes, leukocytes, antigen-presenting cells, antibodies, nanobodies, antigens, markers of inflammation, c-reactive protein (CRP), creatine kinase, calprotectin, lactoferrin, antimicrobial molecules, proteases, cell signaling proteins, cytokines, chemokines, hormones, neurotransmitters, interleukins, vitamins, major histocompatibility (MHC) molecules, complement system molecules, anti-viral molecules, CRISPR-CAS systems, and the like.

As used herein, the term "active agent" comprises drugs, pro-drugs, active pharmaceutical ingredients, nutritional supplements, prebiotics, probiotics, postbiotics, synbiotics, xenobiotics, microbes, immune system molecules, immune system cells, immune system modifiers, dyes, combinations of the above, and the like.

As used herein, the term "stimulus agent" means any substance that is present or processed in some fashion in the GI tract or adjoining organs such as the liver and pancreas, and delivered to the body via ingestion, injection, inhalation, transdermally, or through the device itself. Examples comprise the dietary components, microbes, prebiotics, postbiotics, synbiotics, active agents, xenobiotics, bile acids, or combinations thereof.

As used herein, the term "response" means any change in the biochemical, enzymatic, immunological, metabolic, immunologic, or microbial changes in the host and/or the microbiota that is the result of a stimulus agent and that is measured in the gastrointestinal samples and/or the analytes.

As used herein, the term "fluid movement means" refers to any mechanism or process of moving fluids, comprising pumps and pressure differentials.

Unless otherwise defined, all technical and scientific terms used herein have the same meaning as commonly understood by one of ordinary skill in the art to which this invention belongs. Although methods and materials similar or equivalent to those disclosed herein can be used in the practice of the present invention, suitable methods and materials are disclosed below. In case of conflict, the patent specification, including definitions, will control. In addition, the materials, methods, and examples are illustrative only and not intended to be limiting.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

FIG. 1 illustrates the regions of the human gastrointestinal (GI) tract that are sampled by the device and methods described herein. Food enters stomach 1 where muscles mix the food and liquid with digestive juices. The stomach slowly empties its contents, called chyme, into the duodenum 2, also referred to as the proximal portion of the small intestine. A sharp transition of pH in the GI tract occurs between the stomach, with a pH range of 1.5 to 3.5, and the duodenum, with a pH range of 4 to 7. This sharp pH transition makes this region relatively easy to identify when measuring the pH of the fluid collected by or surrounding the sampling device. The muscles of the small intestine mix food with digestive juices from the pancreas and liver, and push the mixture forward into the jejunum 3, also referred to the as mid portion of the small intestine, for further digestion. The walls of the small intestine absorb the digested nutrients into the bloodstream until the ileum 4, also referred to as the distal portion of the small intestine, is reached. As peristalsis continues, the undigested components of the food move into the cecum, which is the beginning portion of the ascending colon 5, also referred to as the right colon or proximal colon portion of the large intestine where complex carbohydrates are fermented by microbes. Waste products from the digestive process include undigested parts of food, fluid, and older cells from the lining of the GI tract get transferred into the transverse colon 6, also referred to as the mid colon. The descending colon 7, also referred to as the left colon or distal colon portion of the large intestine absorbs water and changes the waste from liquid form into solid stool. Peristalsis helps move the stool into rectum 8 and from there into the toilet during a bowel movement. The pH levels and the linear distance from the mouth to various regions of the GI tract are described more fully in Table 1 below.

TABLE 1 pH of the human GI tract. Ref: Gut, 1988, 29, 1035-1041 and typical linear distance from the mouth to the beginning of each GI region.

| GI region | Mean pH (range) | Distance from mouth to beginning of GI region (cm) |
| --- | --- | --- |
| Stomach | (1.5-3.5) | 45 |
| Duodenum | (4.0-7.0) | 70 |
| Jejunum | 6.6 | 95 |

TABLE 1-continued pH of the human GI tract. Ref: Gut, 1988, 29, 1035-1041 and typical linear distance from the mouth to the beginning of each GI region.

| GI region | Mean pH (range) | Distance from mouth to beginning of GI region (cm) |
| --- | --- | --- |
| Ileum | 7.5 | 200 |
| Right colon | 6.4 | 400 |
| Anus | 7.0 | 500 |

In an initial embodiment, a device for collecting gastrointestinal samples is provided. The device comprises a sampling tube that collects samples throughout the GI tract. The sampling tube comprises a distal end that travels in the GI tract, and a proximal end that stays outside the subject's body while the device is active. The proximal end of the sampling tube is connected to a reservoir. The reservoir, which can be in the form of a tube, sits inside an external enclosure that also comprises the portion of the sampling tube that has not yet been swallowed. The distal portion of the sampling tube comprises an inlet portion with one or more holes that allows gastrointestinal samples to enter the sampling tube.

Figure 2:
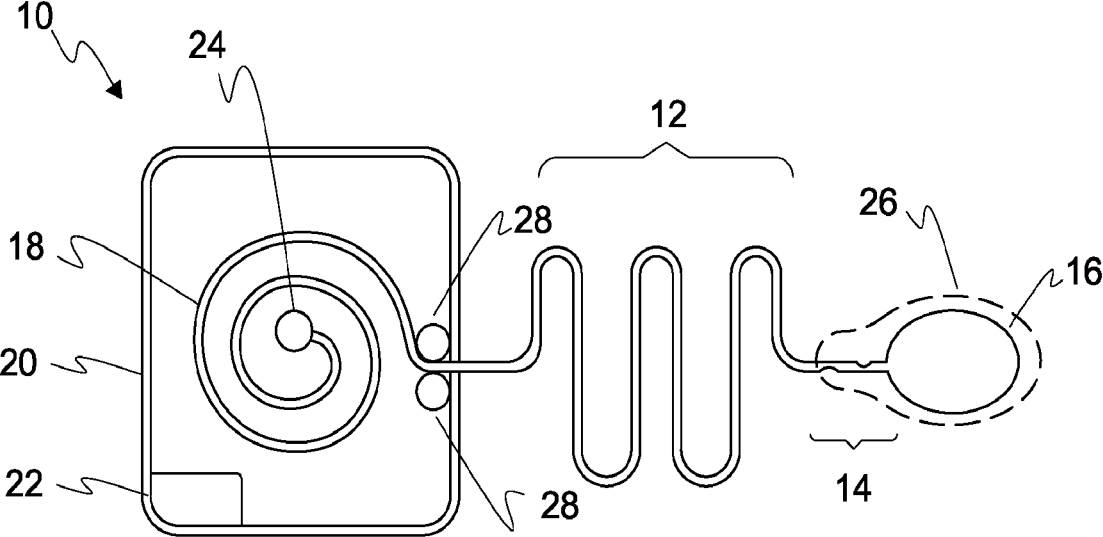
FIG. 2 illustrates the major components of one embodiment of the device.

FIG. 2 illustrates device 10. Sampling tube 12 with inlet portion 14 is connected to head element 16 and surrounded by filtering element 26. Inside external enclosure 20, sampling tube 12 is released or retracted via actuator 28. Sampling tube 12 is connected to reservoir tube 18, which in turn is connected to fluid movement means 24 which is controlled by control unit 22.

Figure 3:
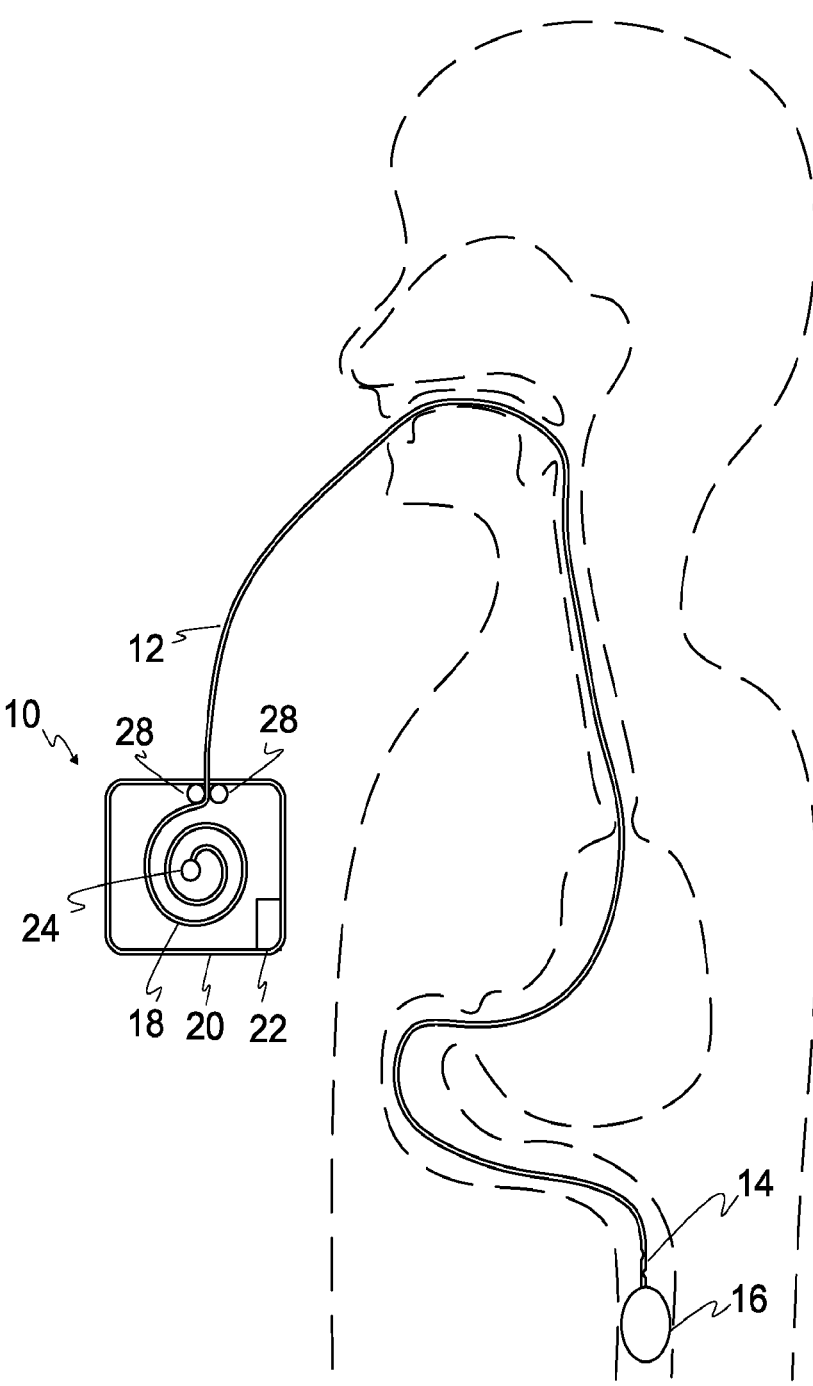
FIG. 3 illustrates one embodiment of the device deployed inside the GI tract of the subject.

FIG. 3 illustrates device 10 deployed inside the GI tract of the subject while external enclosure 20 remains outside the body of the subject.

In an additional embodiment, external enclosure 20 is mounted on the head or around the neck of the user, thereby keeping sampling tube 12 free to enter into the GI tract from the mouth or nose.

In an additional embodiment, the distal portion of sampling tube 12 is connected to head element 16 that increases the peristalsis force acting on sampling tube 12 pulling it through the GI tract.

In an additional embodiment, a string or a portion of sampling tube 12 of sufficient length to allow head element 16 to enter the esophagus is packed inside, wound inside or wound outside head element 16. The packed or wound string or sampling tube exits or unwinds from head element 16 as head element 16 is swallowed. In this manner, the subject does not experience the difficulty of swallowing head element 16 connected to a tube that needs to move through closed lips during the swallowing process. Additionally, the subject does not need to place loose loops of string or sampling tube in their mouth in order to enable the swallowing of head element 16 which can cause gagging. Rather, head element 16 is swallowed with minimal or even no resistance and without pulling on sampling tube 12, since the wound or packed string or portion of sampling tube 12 exits or unwinds from the head portion during the swallowing process without resistance.

In one embodiment, the entire length of sampling tube 12 is wound inside or outside head element 16 or in a separate capsule connected to head element 16.

In a further embodiment, sampling tube 12 is elastically collapsed in the radial direction when wound inside or outside head element 16 to eliminate the internal lumen space. When unwound, sampling tube 12 expands radially to form a patent lumen again. In this manner, the maximum amount of sampling tube is packed into the smallest size head element 16 possible by excluding the gas contained in the lumen of sampling tube 12.

In a further embodiment, only a portion of sampling tube 12 is wound inside or outside head element 16. Once the entire wound or packed portion of the string or sampling tube has exited or unwound from head element 16, head element 16 pulls on sampling tube 12, guiding sampling tube 12 into the esophagus where peristalsis carries head element 16 and the remaining portion of sampling tube 12 further into the GI tract without subject discomfort.

In an additional embodiment, head element 16 and/or a string or portion of sampling tube 12 are both packed into a water-soluble capsule. During the process of swallowing the water-soluble capsule, the packed string or sampling tube emerges from the water-soluble capsule. After swallowing, the water-soluble capsule dissolves and head element 16 acts as a sinker to pull the rest of sampling tube 12 into the GI tract.

In an additional embodiment, head element 16 and/or a string or portion of sampling tube 12 are both packed into an enterically-coated capsule that dissolves at a pH of 5 or higher. During the process of swallowing the water-soluble capsule, the packed string or sampling tube emerges from the enterically-coated capsule only in the intestines, thus avoiding contamination by oropharyngeal and stomach contents.

In an additional embodiment, head element 16 is compressed inside a water-soluble capsule and head element 16 inflates or expands once head element 16 is in the GI tract.

In an additional embodiment, inlet portion 14 of sampling tube 12 is sealed until inlet portion 14 arrives at the initial location to sample in the GI tract. In this manner, oral or nasopharyngeal microbes do not contaminate the initial samples collected further down in the GI tract. Example means of sealing inlet portion 14 comprise plugs that are removable with pressurized fluid or gas from within sampling tube 12, and plugs or covering elements that degrade after a set time period or at a set pH threshold in the GI tract.

In an additional embodiment, a gas or fluid is perfused through sampling tube 12 from the proximal end to the distal end and through inlet portion 14 until inlet portion 14 arrives at the initial location to sample in the GI tract. When at the initial location to sample, the fluid or gas flow is stopped and a sample aspirated through inlet portion 14. In this manner, oral or nasopharyngeal microbes do not enter and contaminate the during transit to the initial sampling location further down in the GI tract.

In an additional embodiment, a control unit in device 10 controls the timing and rate of flow of fluids and/or gases through the sampling and/or dispensing tubes.

In an additional embodiment, at least a portion of sampling tube 12 is packed or wound in an external enclosure kept outside the body of the subject. The portion of sampling tube 12 that is not introduced into the GI tract is kept in external enclosure 20.

In an additional embodiment, the rate of sampling tube 12 that is allowed outside external enclosure 20 is controlled by actuator 28 and/or a control unit. In this manner, the user cannot pull sampling tube 12 out of external enclosure 20 more quickly than sampling tube 12 is supposed to exit due to speed of the peristalsis forces in the GI tract.

In an additional embodiment, the length and dwell time of sampling tube 12 that is allowed outside external enclosure 20 is pre-programmed by a health care professional via a control unit so that a specific region of the GI tract is sampled and/or stimulated. By way of example, the device can be programmed to allow inlet portion 14 of sampling tube 12 to reach the duodenum and then conduct a stimulus agent of releasing a bolus of fat through a dispensing tube and collecting gastrointestinal samples for 20 minutes after the stimulus agent to collect and analyze the bile acids stimulated by fat. At the conclusion of this procedure, sampling tube 12 can be automatically detached from external enclosure 20, or alternatively retracted into external enclosure 20, thereby terminating the procedure.

In an additional embodiment, head element 16 is normally less than 3 mm in diameter in the deflated condition. Head element 16 is inflated to be between 4 mm and 8 mm diameter to enable the swallowing of head element 16. The head element is then further inflated to be between 8 mm and 25 mm in diameter when head element 16 is in the small intestines to increase the peristalsis force acting on head element 16. To not interfere with intestinal flow or enable easy retraction of sampling tube 12, head element 16 is deflated to be less than 8 mm or preferably less than 3 mm in diameter when a gastrointestinal sample is being collected or when head element 16 is in the process of being removed from the body.

In a further embodiment, device 10 releases electrical stimuli to the GI tract in order to accelerate peristalsis, thereby shortening the duration of the procedure.

In a further embodiment, device 10 releases prokinetic agents to the GI tract in order to accelerate peristalsis, thereby shortening the duration of the procedure. Example prokinetic agents comprise benzamide, metoclopramide, cisapride, linaclotide and the like.

In an additional embodiment, head element 16 is in the form of a helix and turns in order to propel sampling tube 12 through the small intestines.

In an additional embodiment, there are two or more head elements 16 that inflate in alternate manner in order to advance through the small intestines. The distal head element 16 is furthest from the mouth and the proximal head element 16 is closest to the mouth. A forward motion cycle comprises the following steps.

i. The distal head element 16, when not inflated, is displaced ahead of the proximal head element 16 which is inflated.

ii. The distal head element 16 is then inflated.

iii. The proximal head element 16 is deflated, and iv. The proximal head element 16 is displaced towards the distal head element 16.

The cycle is then repeated to advance in the small intestines. The cycle can be reversed to move backwards towards the stomach.

In an additional embodiment, the swallowed portion of device 10 is introduced into the subject's body via the mouth.

In an additional embodiment, the swallowed portion of device 10 is introduced into the subject's body via the nasal cavity.

In an additional embodiment, the outer diameter of sampling tube 12 is 2.5 mm or smaller, preferably 2 mm or smaller and most preferably 1 mm or smaller. This diameter tube is much smaller than the 3 mm and greater outer diameter of prior art feeding tubes. The smaller diameter sampling tube of this invention makes the presence of sampling tube 12 in the oral or nasal pharyngeal anatomy completely tolerable for the subject. However, the small diameter requires additional clog prevention means, such as a filtering element comprising a woven mesh, unwoven mesh, or open cell foam. In the present invention and in contrast to prior art gastro or nasopharyngeal feeding tubes, due to the outer diameter of sampling tube 12 being 2.5 mm or less, sampling tube 12 can't support an axial load required to intubate a subject. To avoid irritation of the subject's tissue, primarily in the oropharyngeal areas, sampling tube 12 of this invention is axially flimsy and can't support its own weight when held just ten centimeters away from head element 16. Intubation of sampling tube 12 in this invention requires the subject to swallow head element 16 which is attached to sampling tube 12.

In an additional embodiment, detecting means measure one or more physical, chemical or biological parameters of the sampled fluids and/or the environment in the region of head element 16 and feeds this information to control unit 22.

In an additional embodiment, gastrointestinal samples are extracted continuously as soon as inlet portion 14 of sampling tube 12 has reached the desired initial sampling location in the GI tract.

In an additional embodiment, gastrointestinal samples are extracted intermittently at discrete time points.

In an additional embodiment, gastrointestinal samples are extracted based on the levels of one or more sampling parameters. Sampling parameters comprise pH levels, fluid color, and dissolved gas content of the gastrointestinal fluids. By way of example, when the detecting means detects and increase of pH of the collected samples from less than pH 5 to greater than pH 5 over a period of 1 minute or longer, control unit 22 determines that inlet portion 14 of sampling tube 12 has transitioned from the stomach to the duodenum. If the objective of the study is to sample the duodenum over a period of time, control unit 22 stops the advancement of sampling tube 12 using an external locking mechanism and/or deflates head element 16 to avoid further peristaltic advancement of sampling tube 12. By way of a further example, when the detecting means detects an increase of pH to 7.8 or greater, and/or a decrease in the dissolved oxygen concentration to less than 0.5% and/or an increase in the dissolved hydrogen concentration to above 1% and/or an increase in the dissolved carbon dioxide concentration to above 10% in the collected gastrointestinal fluids, control unit 22 determines that inlet portion 14 of sampling tube 12 is in the ileum.

Additional sampling parameters comprise the distance from the mouth of inlet portion 14 of sampling tube 12 in the GI tract, and/or elapsed time intervals following an event. By way of further example, an event can comprise time of swallowing, time of transition of sampling tube 12 into the small intestines, and time after a stimulus agent such as ingestion of a dietary component, biochemical, microbe, prebiotic, active agent, xenobiotic, or combinations thereof.

In an additional embodiment, gastrointestinal samples move from sampling tube 12 into reservoir tube 18 outside the subject's body and are stored in a linear array. Cross contamination of microbes and analytes along reservoir tube 18 is limited to the rate of diffusion along the length of reservoir tube 18 multiplied by the time interval between sample collection and sample analysis.

In an additional embodiment, a separating agent is introduced into sampling tube 12 and/or reservoir tube 18 at time intervals to create a diffusion barrier of microbes or analytes along the sampling tube 12 and/or reservoir tube 18. Example separating agents comprise a viscous fluid, a water-immiscible fluid such as oil, or a gas.

In an additional embodiment, the introduced separating agent is colored to enable visualization of the delineations of the discrete regions of GI fluids collected.

In an additional embodiment, the samples arriving through sampling tube 12 are diverted into discrete collection chambers, thereby separating the collected GI fluids in discrete sample containers.

In an additional embodiment, a preserving agent is introduced into the collected GI samples inside device 10. The action of the preserving agent comprises preserving the nucleic acids, stopping enzymatic activity in the collected GI samples or a cryoprotectant for the collected cells to keep them viable for culturing. Examples of preserving agents comprise RNA Later®, DNA/RNA Shield®, TRIzol®, ammonium sulfate, sugars, glycerol, and the like.

In an additional embodiment, the preserving agent is introduced into the flow of the GI samples through the sampling tube 12 and/or reservoir tube 18.

In an additional embodiment, the preserving agent flows through a tube and is combined with the GI fluids flowing through the sampling tube 12 and/or reservoir tube 18 via a tube junction under the control of a pressure source and/or valve.

In an additional embodiment, the preserving agent is a solution that is pre-loaded into reservoir tube 18 and/or the collection chambers.

In an additional embodiment, the preserving agent is dehydrated. The preserving agent is rehydrated when coming into contact with the GI fluid.

In an additional embodiment, reservoir tube 18 is an extension of sampling tube 12.

In an additional embodiment, the inner diameter of reservoir tube 18 is greater than the inner diameter of sampling tube 12 in order to minimize the length of reservoir tube 18 required to store a given volume of gastrointestinal samples.

In an additional embodiment, the linear array of gastrointestinal samples stored in reservoir tube 18 is a recapitulation of the linear order of the fluids present inside the GI tract.

In an additional embodiment, each sample in the linear array in reservoir tube 18 or in each collection chamber is associated with the length of sampling tube 12 ingested at the time of sampling, thereby allowing for determination of the region of the GI tract that the sample was collected from.

In an additional embodiment, the microbes in the gastrointestinal samples are stored in reservoir tube 18 in the same aerobic or anaerobic condition as their natural environment in the GI tract.

In an additional embodiment, the flow of gastrointestinal samples into the sampling tube 12 and/or reservoir tube 18 is at least partially driven by capillary pressure.

In an additional embodiment, the flow of gastrointestinal samples into the sampling tube 12 and reservoir tube 18 is at least partially driven by gravity.

In an additional embodiment, the flow of gastrointestinal samples into the sampling tube 12 and reservoir tube 18 is at least partially driven by the higher pressure of the fluids in the GI tract relative to the atmospheric pressure outside the subject's body.

In an additional embodiment, the end of reservoir tube 18 furthest from sampling tube 12 vents to atmospheric pressure during sample collection.

In an additional embodiment, an evacuated chamber provides the vacuum force that drives samples into sampling tube 12.

In an additional embodiment, the evacuated chamber is reservoir tube 18.

In an additional embodiment, the evacuated chamber is the collection chamber.

In an additional embodiment, the rupture of a membrane or septum covering the evacuated chamber drives the vacuum-driven flow of GI fluids through sampling tube 12 into a collection chamber.

In an additional embodiment, the degradation of a pH-sensitive element blocking inlet portion 14 of sampling tube 12 initiates the vacuum-driven flow of GI fluids into sampling tube 12. By way of example, a pH-sensitive capsule around head element 16 including inlet portion 14 of sampling tube 12 degrades at pH 5 or greater, thereby initiating sampling when head element 16 is in the duodenum.

In an additional embodiment, the rate of flow of GI fluids into sampling tube 12 is controlled by a flow resistance element. Examples of flow resistance elements comprise a valve or an orifice.

In an additional embodiment, the actuation of one of more valves controls the flow of samples into sampling tube 12.

In an additional embodiment, the flow of gastrointestinal samples into the sampling tube 12 and/or reservoir tube 18 is at least partially driven by the pressure created by peristaltic contractions of the GI tract muscles.

In an additional embodiment, the flow of gastrointestinal samples into sampling tube 12 is driven by a pump.

In an additional embodiment, head element 16 comprises a pump that forces GI fluids through sampling tube 12 and out of the body using positive pressure or direct displacement.

In an additional embodiment, power to the pump in head element 16 is stored in batteries inside head element 16.

In an additional embodiment, power to the pump is transferred from outside the body using conductive elements that run alongside or inside sampling tube 12.

In an additional embodiment, a tube connects a pressure source outside the body to an inflatable bladder inside a pump chamber inside head element 16. Deflation of the bladder forces fluids from the GI tract through a one-way valve into the pump chamber. Inflation of the bladder forces fluids from the pump chamber through a one-way valve through sampling tube 12 and into a collection chamber. An advantage of this embodiment is that the power and pressure sources that drive this pump are outside the body. Oscillating hydraulic pressure transferred through a tube into the body is used to drive the pump. Furthermore, the pressure differential driving the flow of the relatively viscous GI fluids through the long sampling tube can be greater than atmospheric pressure, which is the upper limit of a vacuum-based system that applies vacuum to the proximal end of sampling tube 12. Vacuum can also collapse the lumen of a thin and flexible sampling tube along its length.

In a further embodiment, head element 16 comprises two nested balloons, an inner and outer balloon. The outer balloon comprises a one-way valve that only allows fluids into the balloon. The outer balloon is fluidly connected to sampling tube 12, which also has a one-way valve allowing flow of samples only towards the proximal end of sampling tube 12. The inner balloon is fluidly connected to a controlled source of hydraulic pressure. When the inner balloon is expanded inside the outer balloon, the inner balloon forces any fluids between the two balloon out of the proximal end of sampling tube 12 due to the one-way valves limiting flow in that direction. When the inner balloon is collapsed, fluid is drawn into the space between the two balloons through the one-way valve on the outer balloon. This fluid is then transferred out of the body at the next expansion of the inner balloon. In this manner, head element 16 is controllable in size to enable peristalsis to carry sampling tube 12 through the GI tract, and also serves as a pumping element acting as fluid movement means 24 to drive GI fluids out of sampling tube 12 into the collection chamber. This embodiment only requires two fluid channels in and out of the body, which could be two coaxial tubes or a single multi lumen tube.

In a further embodiment, a tube connects a pressure source outside the body to a piston elastically-biased to pull fluids from the GI tract through a one-way valve into a pump chamber. Fluid pressure delivered from outside the body to the piston overcomes the elastic bias and forces the piston to push fluids from the pump chamber via a one-way valve through sampling tube 12 and into a collection chamber.

In an additional embodiment, the flow of gastrointestinal samples into sampling tube 12 occurs in an oscillatory manner wherein fluid is driven both in and out of inlet portion 14 of sampling tube with a net bias in favor of inflow. In this manner, particles blocking the sampling open are dislodged and clogging of sampling tube 12 is avoided.

In an additional embodiment, the flow of gastrointestinal samples into sampling tube 12 is automatically reversed for a brief period to clear a blockage as soon as lack of adequate forward flow of gastrointestinal samples inside sampling tube is detected by a flow sensor.

In an additional embodiment, inlet portion 14 of sampling tube 12 is surrounded by a filtering element with a pore size smaller than the inner diameter of sampling tube 12.

In an additional embodiment, inlet portion 14 of sampling tube 12 is surrounded by a cage that prevents the mucosal surface of the GI tract from collapsing on inlet portion 14 of sampling tube 12 and blocking flow therein.

In an additional embodiment that increases the surface area of filtering element 26, at least a portion of head element 16 and inlet portion 14 of sampling tube 12 are surrounded by filtering element 26 with a pore size smaller than the inner diameter of sampling tube 12.

In an additional embodiment, the dead volume between filtering element 26 and inlet portion 14 of sampling tube 12 is 250 microliters or less in order to minimize dead volume of gastrointestinal fluids in the region of inlet portion 14. In this manner, less trapped fluid is carried over between sampling sites in the GI tract and a more representative sample of GI fluids is collected.

In an additional embodiment, the macroscopic surface area of filtering element 26 when laid out as a flat sheet is at least 0.25 square centimeter in order to allow sufficient number of pores to prevent clogging of sampling tube 12.

In an additional embodiment, filtering element 26 covers at least a portion of the circumferential surface of a capsule-shaped head element 16 to sample from the mucus and/or wall of the GI tract where the microbe population may be different from the microbes in the lumen of the GI tract.

In an additional embodiment, inlet portion 14 of sampling tube 12 is placed at the circumferential surface of head element 16 to sample from the mucus and/or wall of the GI tract where the microbe population may be different from the microbes in the lumen of the GI tract.

In an additional embodiment, inlet portion 14 of sampling tube 12 is elastically biased outward from head element 16 in the radial direction of the GI lumen in order to sample from the mucus and/or wall of the GI tract where the microbe population may be different from the microbes in the lumen of the GI tract.

In an additional embodiment, head element 16 mechanically degrades after being present in the GI tract for a predetermined time range. Examples of mechanical degradation comprise dissolving, eroding, weakening, collapsing and disintegrating. In this manner, the likelihood of retaining head element 16 in the GI tract due to a stricture is greatly reduced.

In an additional embodiment, head element 16 is connected to sampling tube 12 by a connector or adhesive.

In an additional embodiment, the connector or adhesive between sampling tube 12 and head element 16 detaches with a pulling force on the portion of sampling tube 12 outside of the subject's body.

In an additional embodiment, the connector or adhesive between sampling tube 12 and head element 16 mechanically degrades after being present in the GI tract for a predetermined time range. Examples of mechanical degradation comprise dissolving, weakening, eroding, and disintegrating. By way of example, the connector or adhesive between sampling tube 12 and head element 16 dissolves within 12 hours after sampling tube 12 is swallowed, which allows sufficient time for inlet portion 14 of sampling tube to reach the ascending colon and GI samples to be collected throughout a 12 hour transit time.

In an additional embodiment, the connector or adhesive between sampling tube 12 and head element 16 enzymatically degrades after being present in the colon for a predetermined time range and thereby disconnects sampling tube 12 from head element 16 in the colon at the conclusion of the gastrointestinal sampling process. The colon is known to consist of species of anaerobic microorganisms such as *Clostridium* species. These bacteria contain hydrolytic and reductive metabolizing enzymes. Example materials that are preferentially degraded by the anaerobic microbes present in the colon comprise guar gum, chitosan, pectin, calcium alginate, lactulose, carboxymethyl cellulose, high-amylose maize starch and other polysaccharides, including derivatives and combinations thereof.

In a further embodiment, head element 16 is connected to sampling tube 12 by a fuse element that is detachable via electrical current.

In a further embodiment, head element 16 is inflatable and detaches from sampling tube 12 at a certain minimum pressure of inflation of head element 16.

In an additional embodiment, head element 16 is a thin wall envelope that is inflated with gas, fluid or liquid metal via a tube after head element 16 passes into or out of the stomach.

In an additional embodiment, head element 16 is a thin envelope formed around sampling tube 12. The head element is expanded radially via inflation with gas, fluid or liquid metal through a tube. When inlet portion 14 of sampling tube 12 has reached the desired sampling location in the GI tract, and/or during the sampling event itself, the inflatable head element is deflated and shrunk radially to again form a thin envelop around sampling tube 12 so that head element 16 will not interfere with the GI tract motility patterns and the flow of gastrointestinal samples through the GI tract.

In an additional embodiment, before sampling tube 12 is withdrawn from the mouth or released to be eliminated in the stool, head element 16 is deflated to prevent interference of head element 16 in the removal process.

In an additional embodiment, head element 16 comprises a swelling polymer that grows in size when exposed to the moisture of the GI tract. In this manner, the size of head element 16 that needs to be swallowed is minimized. The head element, which serves as a sinker that is acted on by peristalsis, grows in size and effectiveness only after head element 16 has been swallowed. An example swelling polymer comprises sodium acrylate.

In an additional embodiment, a method is provided to minimize the dwell time of head element 16 in the stomach of a user. Sampling tube 12 and head element 16 are swallowed by the user after a fast of at least 8 hours and within 2 hours, or preferably 1 hour, of the consumption of a test meal of 250 calories or less, or preferably 150 calories or less, and then no more food is consumed for at least 2 hours. This method minimizes the time that head element 16 is resident in the stomach and hence that device 10 needs to be in use. The migrating motor complex that empties head element 16 from the stomach is likely to be triggered within an hour of the consumption of a test meal of 250 or 150 calories or less when taken after an extended fast.

In an additional embodiment, sampling tube 12 emerges from external enclosure 20 as sampling tube 12 is pulled further into the GI tract.

In an additional embodiment, the distance traveled by inlet portion 14 of sampling tube 12 in the GI tract is computed in control unit 22 by measuring the length of sampling tube that emerges from external enclosure 20. The velocity profile of inlet portion 14 of sampling tube 12 through the GI tract is computed in control unit 22 by combining this distance information with elapsed time since sampling tube 12 was ingested. Means of measuring the amount of sampling tube that emerges from external enclosure 20 comprise optical detection of markings on sampling tube 12, and rotary encoders on spools or rollers in contact with sampling tube 12 inside external enclosure 20.

In an additional embodiment, detecting means outside the subject's body or in a portion of device 10 within the subject's body measure a parameter of the gastrointestinal fluids as they flow into reservoir tube 18 and this information is transferred to a control unit. Example parameters that are measured comprise pH, concentration of dissolved gases, color, inflammatory markers, biochemical and microbial content.

In an additional embodiment, the measured parameters are correlated to the computed distance of inlet portion 14 of sampling tube 12 and time stamped in control unit 22 in order to determine the location and timing of the occurrence of the measured parameter in the GI tract. An adjustment is made for the time it takes for the gastrointestinal fluids to flow between inlet portion 14 of sampling tube 12 to the detecting means.

By way of example, a linear map of inflammation along the GI tract is created by correlating the concentration of inflammatory markers that were collected along the GI tract with the inferred location of inlet portion 14 of device 10 in the GI tract at the time the inflammatory markers were collected.

By way of an additional example, the location of bleeding in the GI tract can be identified by correlating the first detected elevation of a blood marker in the samples collected along the GI tract with the inferred location of inlet portion 14 of device 10 in the GI tract at the time the first elevated blood marker was detected. The collected gastrointestinal fluids that are stored as a linear array in reservoir tube 18 represent the linear order of analytes, such as blood, in the gastrointestinal fluids. In this manner, a clinician can identify the location, anatomical distribution and intensity gradient of a physiological, immunological, microbial, metabolic or biochemical phenomenon of interest occurring anywhere along the GI tract.

In an additional embodiment, sampling is initiated and/or stopped by control unit 22 based on one or more of the measured parameters above.

In an additional embodiment, gastrointestinal fluids are constantly or regularly monitored by the detecting means and collected in a waste container inside external enclosure 20. When control unit 22 detects that a sampling parameter warrants sample collection, the gastrointestinal fluids are diverted into a reservoir tube or collection chamber and stored as a gastrointestinal sample, along with a time and distance stamp indicating when and where in the GI tract the gastrointestinal samples were collected.

In an additional embodiment, detachment of head element 16 from sampling tube 12 or deflation of head element 16 is initiated by control unit 22 based on one or more of the sampling parameters. By way of example, after measuring a pH drop from greater than pH 7.5 to below pH 6 of the collected gastrointestinal samples, combined with an elapsed small bowel transit time of at least 2 hours, control unit 22 determines that inlet portion 14 of sampling tube 12 has reached the ascending colon. After collecting a sample from the ascending colon, control unit 22 activates actuator 28 to withdraw sampling tube 12 from the subject's body at a maximum withdrawal force of 0.5 Newtons in order to minimize the chance of small bowel plication, tissue damage, or perforation. Example actuators comprise motors and springs. If head element 16 is still attached, control unit 22 also activates actuator 28 to disconnect or deflate head element 16.

In an additional embodiment, sampling tube 12 is sealed in external enclosure 20 after sampling is complete. Example sealing means comprise pinching or kinking sampling tube 12 via actuator 28 and the closing of a valve.

In an additional embodiment, actuator 28 element in external enclosure 20 cuts sampling tube 12 allowing sampling tube 12 to detach from external enclosure 20, and to be swallowed after completion of the gastrointestinal sampling. The detached sampling tube is then eliminated in the feces.

In an additional embodiment, sampling tube 12, which is up to 5 meters long, comprises shorter sections that are connected with linker elements that mechanically degrade in moisture over a preset time period. In this manner, sampling tube 12 has a contiguous open lumen while sampling gastrointestinal fluids, but then sampling tube 12 breaks into shorter segments in the GI tract after the sampling is finished and before a bowel movement. In this manner, sampling tube 12 does not emerge from the anus as a long tube that may only partially evacuate in a single bowel movement. Rather, sampling tube 12 emerges from the anus in short sections that are more likely to be evacuated in a single bowel movement.

In an additional embodiment, sampling tube 12 has radial protrusions at linear intervals to assist in advancing sampling tube 12 through the GI tract via peristalsis.

In an additional embodiment, the radial protrusions dissolve over time or lose friction with sampling tube 12 when exposed to moisture. In this manner, the radial protrusions do not interfere with the withdrawal of sampling tube 12 from the body.

In an additional embodiment, the radial protrusions are made of a swellable polymer. The radial protrusions are ingested in the dry and shrunken state and swell in the GI tract.

In an additional embodiment, gastrointestinal fluids are collected and analyzed in order to measure the response in the GI tract to a stimulus agent. Examples of stimulus agent comprise ingestion of dietary components, biochemicals, microbes, prebiotics, active agents, xenobiotics, or combinations thereof. The stimulus agent can be injected, ingested via the mouth, or introduced through sampling tube 12 or a separate dispensing tube of device 10.

In an additional embodiment, the amount of ingested stimulus agent and the timing of ingestion are coordinated so that the ingested stimulus agent arrives at the region of interest of the GI tract at the same time that device 10 is collecting samples in the GI region of interest. Different stimulus agent can be implemented sequentially so that the sampling device, which is being propelled through the GI tract via peristalsis, measures the response to these stimulus agents in successive regions of the GI tract in real time.

In an additional embodiment, a method of prompting a subject to ingest a stimulus agent in order to collect a gastrointestinal sample reflecting the subject's response to the stimulus agent comprises:

i. providing a sampling device comprising a detecting means, a control unit, and a sampling tube that comprises an inlet portion, ii. introducing inlet portion 14 of sampling tube 12 to the GI tract of the subject, iii. allowing inlet portion 14 of sampling tube 12 to advance through the gastrointestinal tract under peristaltic forces, iv. collecting gastrointestinal fluids through inlet portion 14, v. using the detecting means to measure one or more sampling parameters. Example sampling parameters comprise elapsed time, pH of the collected gastrointestinal fluids, color of the collected gastrointestinal fluids, or distance between the mouth of the user and inlet portion 14 of sampling tube 12 in the gastrointestinal tract, vi. using control unit 22 to infer the anatomical position and/or velocity of inlet portion 14 of sampling tube in the gastrointestinal tract from the one or more sampling parameters, vii. using control unit 22 to prompt the user to ingest the stimulus agent by mouth when inlet portion 14 of sampling tube 12 is within a preset time or distance of the gastrointestinal region of interest, and viii. collecting a gastrointestinal sample through inlet portion 14 when both the ingested stimulus agent and inlet portion 14 of sampling tube 12 have reached the gastrointestinal region of interest.

In an additional embodiment, step vii above is replaced with a stimulus agent that is introduced through sampling tube 12 or a separate dispensing tube into the GI tract.

In an additional embodiment, device 10 comprises one or more stimulus agents in storage compartments that are introduced into the GI tract via sampling tube 12 or a separate dispensing tube.

In an additional embodiment, the advancement of sampling tube 12 in the GI tract is temporarily stopped by control unit 22 using actuator 28 in external enclosure 20. In this manner, gastrointestinal samples are collected from one region of the GI tract for an extended period of time. The location where the advancement is stopped is controlled by control unit 22 based on a pre-programmed setting, or triggered by one or more sampling parameters that are measured in real time.

In an additional embodiment, the advancement of sampling tube 12 in the GI tract is temporarily stopped by control unit 22 in GI region of interest until a stimulus agent has passed inlet portion 14 of sampling tube 12. One or more sampling parameters that are known to be altered by the stimulus agent are measured at baseline before the stimulus agent has reached inlet portion 14 of sampling tube 12. The same sampling parameters are measured while the stimulus agent has reached inlet portion 14 of sampling tube 12, and for a period of time thereafter. Once the sampling parameters have returned to baseline, indicating that the stimulus agent has passed inlet portion 14 of sampling tube 12, then control unit 22 releases sampling tube 12 to continue progressing through the GI tract. The stopping and sampling procedures are repeated at additional locations in the GI tract. Alternatively, once the sampling parameters have returned to baseline, control unit 22 activates actuator 28 that withdraws sampling tube 12 from the body or detaches sampling tube 12 from external enclosure 20 to terminate the sampling procedure.

The main biotransformation pathway of active agents and xenobiotics by humans involves oxidation and conjugation. The major pathways of metabolism by microbes, however, are reduction and deconjugation. Active agents and xenobiotics are glucuronidated by the intestine and/or the liver before they are transported into the bile and excreted into the intestine, where they are further modified by the gut microbiota. The metabolites of drugs and other xenobiotics formed by the intestinal microbiota may have altered toxicity relative to human modifications. In one embodiment, an active agent or xenobiotic is administered to a subject via any of the usual food or drug delivery modalities, or directly through the sampling or dispensing tube of the present invention. Gastrointestinal samples are collected from the GI tract before and/or after administration of the active agent or xenobiotic to assess the modification, transformation or metabolism to the active agent or xenobiotic, as well as the microbes that are responsible for the observed modification or metabolism. Example active agents whose pharmacology and toxicology are thought to be modified by GI microbiota comprise salicylazosulfapridine, digoxin, 1-dopa, acetaminophen, caffeic acid, phosphatidyl choline, carnitine, sorivudine, irinotecan, nonsteroidal anti-inflammatory drugs, heterocyclic amines, melamine, nitrazepam, and lovastatin.

In another embodiment, a method of optimizing drug selection, formulation or dose comprises dosing a subject with one or more candidate drugs or dosing levels, collecting gastrointestinal samples before and after drug administration, and determining the favorable drug, drug formulation or dosing level based on analyzing the collected gastrointestinal samples that have been altered by the drug or drug metabolites present in the GI tract. Example analyses comprise presence or absence of specific drug metabolites, microbes, and host molecules created or depleted in response to the drug.

In another embodiment, device 10 measures a parameter of interest throughout the GI tract and control unit 22 releases an active agent when such a parameter is detected at an appropriate level. By way of example, if inflammation markers are detected by device 10 in certain regions of the GI tract during the normal peristaltic-driven transit of device 10 through the GI tract, then control unit 22 can deliver an anti-inflammatory active agent in those regions of the GI tract. In this manner, the local concentration of the active agent is maximized in the regions of the GI tract where device 10 detects inflammation.

In another embodiment, device 10 collects gastrointestinal samples through sampling tube 12 and also delivers active agents through the same sampling tube by reversing the direction of the flow of fluids though sampling tube 12. In this manner, a single sampling tube 12 fulfills the functions of the sampling and dispensing functions, thereby minimizing the cross-sectional profile of the tube that is swallowed by the subject which increases tolerability.

Molecular-sized dietary stimulus agents ingested via the mouth advance through the GI tract at a much faster rate than the pill-sized head element of sampling tube 12. Small batches of simple nutrients pass the small intestine from the duodenum to the ileum in an hour or so, while head element 16 of device 10 can take up to 3 to 6 hours to be propelled along the same distance. In a further embodiment, this mismatch of transit velocities is utilized to stimulate the GI tract sequentially and to measure the response to that stimulus agent at multiple points along the GI tract without interfering in the natural advancement rate of device 10 through the GI tract. In this manner, the response to multiple stimulus agent can be measured throughout the course of a single 4 to 12-hour sampling procedure.

In a further embodiment, in order to minimize the gastric emptying time and reach the small intestines within 30 to 120 minutes from ingestion, the dietary stimulus agent is digested in a blended or liquid consistency and limited to 100 grams or less, preferably 50 grams or less, or more preferably 25 grams or less. Gastric emptying time is dramatically reduced when ingested food has a liquid consistency, ingested in volumes of less than 100 grams, and while the subject has an empty stomach after a fast of at least 8 hours.

By way of example, stimulus agents can comprise the major dietary components of carbohydrates, proteins, fats, vitamins, minerals, and fiber. The processing of these dietary components in the GI tract is a result of the combined actions of host and microbial metabolism. By stimulating the GI tract in specific regions and with known dietary components separately, and analyzing the resulting metabolic byproducts contained in the local GI samples collected after stimulation, abnormalities of metabolism and processing can be readily identified, along with the microbes and enzymes responsible for these abnormalities. Corrective actions, such as dietary changes, or addition/deletion of specific microbial species can be performed based on these results.

A major challenge in nutritional science is to isolate the effect of various food components on the host and the microbiota in the gut. In a further embodiment, the dietary stimulus agent is predominantly a single nutrient group isolated from other nutrients groups. Example nutrient groups comprise simple carbohydrates, proteins, fats and complex carbohydrates such as dietary fiber. In this manner, it is easier to correlate the host and microbiota response in the GI tract to a single stimulus agent, versus attempting to measure the response to a complex nutrient stimulus agent comprising more than one nutrient group ingested at the same time, as is typical in a standard meal. The different nutrient groups can be used as sequential stimulus agent. Ingestion of each nutrient group is separated from another nutrient group by at least 30 minutes, and preferably 60 minutes. This separation allows for the stomach to fully empty a liquid or blended nutrient stimulus agent of 100 grams or less, preferably 50 grams or less, and more preferably 25 grams or less. An emptying of the stomach between ingestion of a nutrient component prevents the responses to sequential ingested stimulus agent from overlapping or interfering with one another.

In a further embodiment, a dietary stimulus agent where 50% or more of the stimulus agent comprises the fat nutrient group is delivered directly by device 10 or ingested by the subject after being prompted by device 10 when one or more of the sampling parameters indicate inlet portion 14 of sampling tube 12 is in the duodenum. The fat stimulus agent causes bile acid release, thus ensuring that a comprehensive gastrointestinal sample of a subject's primary bile are collected for further analysis. Gastrointestinal samples from this region collected in this manner also capture the dynamics of fat absorption, which is important for diseases such as obesity.

In a further embodiment, a dietary stimulus agent where 50% or more of the stimulus agent comprises the fat nutrient group is delivered directly by device 10 or ingested by the subject after being prompted by device 10 when one or more of the sampling parameters indicate inlet portion 14 of sampling tube 12 is in or near the jejunum or ileum. The microbiota in the small intestine, and primarily the jejunum and ileum, convert primary bile acids to deconjugated and secondary bile acids with important regulatory, immunological, signaling, and antimicrobial functions. The fat stimulus agent causes bile acid release, thus ensuring that a comprehensive gastrointestinal sample of a subject's secondary and deconjugated bile acids are collected for further analysis.

In a further embodiment, a dietary stimulus agent where 50% or more of the stimulus agent comprises the simple carbohydrate nutrient group is delivered directly by device 10 or ingested by the subject after being prompted by device 10 when one or more of the sampling parameters indicate that inlet portion 14 of sampling tube 12 is in or near the first section of the jejunum. The carbohydrate stimulus agent starts a process of host and microbial enzymes extracting energy from the simple carbohydrates, such as fructose and mannose, through glycolysis/gluconeogenesis. Gastrointestinal samples from this region collected in this manner capture the dynamics of sugar absorption, which is important for diseases such as diabetes.

In a further embodiment, a dietary stimulus agent where 50% or more of the stimulus agent comprises the protein nutrient group is delivered directly by device 10 or ingested by the subject after being prompted by device 10 when one or more of the sampling parameters indicate that inlet portion 14 of sampling tube 12 is in or near the middle section of the jejunum. The protein stimulus agent starts a process of protease enzymes breaking down proteins into amino acids. Gastrointestinal samples from this region collected in this manner capture the dynamics of protein digestion, which is important for metabolic diseases.

In a further embodiment, a dietary stimulus agent where 50% or more of the stimulus agent comprises the complex carbohydrate group such as dietary fiber is delivered directly by device 10 or ingested by the subject after being prompted by device when one or more of the sampling parameters indicate that inlet portion 14 of sampling tube 12 is in or near the ileum or ascending colon. The fiber stimulus agent starts a process of fermentation that breaks down the fibers into short chain fatty acids. Gastrointestinal samples from this region collected in this manner capture the dynamics of short chain fatty acid digestion, which is important for diseases such as cancer and neurological conditions.

Table 2 below provides an example timeline of a 5-hour stimulus agent/response sampling sequence using the embodiments described above. The two sampling parameters used to infer the location of inlet portion 14 of device 10 in the GI tract are distance and pH. The distance sampling parameter is the length of sampling tube that has been swallowed as measured directly or as measured by the amount of sampling tube that has exited external enclosure 20, indicating the distance between the mouth and the GI region of interest. The pH sampling parameter is the pH of the collected gastrointestinal fluids as measured in real time by the detecting means and compared by control unit 22 of device 10 to the expected pH transitions between the GI regions as shown in Table 1. The distance and pH parameters are used to infer the location of inlet portion 14 of the sampling device. The time delay is the time between ingestion of the dietary stimulus agent and the time of collection of a sample in the GI tract representing the response to the ingested stimulus agent. This time delay correlates to the time calculated by control unit 22 of device 10 for the ingested nutrient stimulus agent to travel through the GI tract and reach the sampling device, which is also traveling through the GI tract, but at a slower velocity than the stimulus agent.

TABLE 2

Example timeline of a sequence of dietary stimulus agent coupled to a sampling sequence that measures the response of the GI tract to each stimulus agent.

| Time after device ingestion (min) | Measured Distance from lips (cm) | Measured pH | Inferred location of sampling device | Dietary stimulus agent | Sample GI fluids collected | Time delay (min) |
|---|---|---|---|---|---|---|
| 0 | 10 | n/a | Outside mouth | n/a | n/a | n/a |
| 10 | 65 | 1.2 | Stomach | n/a | Stomach | n/a |
| 60 | 75 | 5.0 | Duodenum | Fat stimulus agent | n/a | n/a |
| 75 | 85 | 5.5 | Duodenum | n/a | Duodenal response to fat | 15 |
| 90 | 105 | 6.0 | Proximal jejunum | Simple carbohydrate stimulus agent | n/a | n/a |
| 120 | 160 | 6.5 | Mid jejunum | Protein stimulus agent | Jejunal response to simple carbohydrates | 30 |
| 180 | 200 | 7.0 | Distal jejenum | Fiber stimulus agent | Jejunal response to protein | 60 |
| 240 | 300 | 7.5 | Ileum | n/a | Ileum | 60 |

TABLE 2-continued

Example timeline of a sequence of dietary stimulus agent coupled to a sampling
sequence that measures the response of the GI tract to each stimulus agent.

| Time after device ingestion (min) | Measured Distance from lips (cm) | Measured pH | Inferred location of sampling device | Dietary stimulus agent | Sample GI fluids collected | Time delay (min) |
|---|---|---|---|---|---|---|
| 300 | 450 | 6.5 | Ascending colon | n/a | response to fiber Ascending colon response to fiber | 120 |

In a further embodiment, some injected or IV-administered drugs are glucuronidated by the liver, and then they are transported into the bile and excreted into the intestine where they are deconjugated by gut microbiota. Collecting these drug metabolites along with the microbes that are responsible for the biochemical transformations is useful for proper drug selection, drug dosing, or to guide the selective addition or deletion of microbial strains.

In a further embodiment, antibiotics are introduced into a subject by the traditional oral or IV dosing means or via the sampling or dispensing tube of the present invention. The effect of the antibiotic is determined by collecting and analyzing the viable microbial populations before and after the antibiotic administration.

In a further embodiment, a microbe and/or prebiotic can be delivered to a region of the GI tract through sampling tube 12, and then after a time delay, GI luminal contents can be collected via the same sampling tube to determine the response of the host or gut microbiota to the stimulating microbe and/or prebiotic.

By way of further example, one of more bile acids can be introduced into the GI tract and the transformed bile acid, along with the microbes that conducted the biochemical transformation are collected and analyzed. In such a manner, disorders of bile acid synthesis processing can be identified and treated.

In a further embodiment, the duration of the GI tract response to a stimulus agent is measured optically. The baseline color of gastrointestinal fluids from the stomach are clear, turning to pink when food is being digested and returning to a baseline of clear when the stomach is empty again. The baseline color of gastrointestinal fluids from the small intestines when no nutrients are present is yellow, turning to green when bile or nutrients are present as a result of an ingested dietary stimulus agent, and then returning back to the baseline yellow color after the dietary stimulus agent has passed. Likewise, the baseline color of gastrointestinal fluids from the cecum and ascending colon is green turning to brown based on the time the ingested stimulus agent has been in the cecum and ascending colon, returning to the baseline green color when the cecum and ascending colon receive a new batch of effluent from the ileum.

In a further embodiment, control unit 22 of device 10 will notify or prompt the subject at the optimal time to ingest a dietary stimulus agent based on the inferred location and calculated velocity of inlet portion 14 of sampling tube 12 in the GI tract, and the predicted time required for the dietary stimulus agent to transit the GI tract. In this manner, control unit 22 calculates a time delay that ensures that the ingested dietary stimulus agent will arrive at the desired region of the GI tract at the same time as inlet portion 14 of sampling tube 12. The time delay is the time between the ingestion of the dietary stimulus agent and the collection of gastrointestinal samples representing the response. By way of example, device 10 can be programmed such that a response to a fat stimulus agent will be collected in the duodenum with a time delay of approximately 15 minutes, a response to simple carbohydrate and protein stimulus agent will be collected in the jejunum with a time delay of approximately 60 minutes, and a response to a fiber stimulus agent will be collected in the ileum and ascending colon with a time delay of up to 120 minutes.

In a further embodiment, a stimulus agent is introduced through an opening in sampling tube 12 that is located at a known distance proximal to inlet portion 14. A gastrointestinal sample is collected from inlet portion 14 of sampling tube 12 at a time subsequent to when the stimulus agent is introduced, thus capturing any alterations to the stimulus agent or luminal contents of the GI tract that occurred on the way between the injection point of the stimulus agent and the inlet portion 14 of sampling tube 12.

In a further embodiment, device 10 comprises an untethered capsule that captures the response of the GI tract to a stimulus agent in the region of interest. The capsule is ingested at a known time difference from the stimulus agent to ensure that collection of the response to the stimulus agent occurs in a predetermined target GI region.

Since the largest source of variability in determining the location of an untethered capsule in the GI tract is the gastric emptying time, in a further embodiment, the capsule device notifies the subject when the capsule has passed into the duodenum via wireless or audible communication means based on a pH change from a range of pH 1-3 to a range of pH 5-6. The transit time of the capsule through the small intestine and into the colon is more predictable than gastric emptying time. The prompt to the subject to ingest the stimulus agent is timed by control unit 22 of device 10 so that the ingested stimulus agent and the capsule meet in the GI region of interest and a gastrointestinal sample is collected therein.

In a further embodiment, a plurality of untethered device capsules is ingested at one time or at known time intervals, wherein each capsule device is designed to sample a different region of the GI tract.

In a further embodiment, an untethered capsule-shaped device comprises both a stimulus agent and a collecting chamber. The stimulus agent is released into the GI tract by the capsule-shaped device, and at the same time or with a set time delay, the collecting member collects gastrointestinal samples that when analyzed confirm the release of the stimulus agent by recapturing a portion of the stimulus agent, determine the response of the host or the gut microbiota to the stimulus agent, and establish the location in the GI tract where the stimulus agent was released and the sample was collected from. In this embodiment, the stimulus agent and the collection of the gastrointestinal sample occur in close proximity and at the same time or with a set time delay to allow for the stimulus to be processed in the GI tract.

In a further embodiment, after dispensing the stimulus agent to the GI tract, the volume inside capsule-shaped device that stored the stimulus agent is utilized to store the collected gastrointestinal samples that represent the response. In this manner, a capsule is swallowed that comprises a stimulus agent, and the same capsule when recovered from the stool comprises the gastrointestinal samples representing the response to the stimulus agent as well as some amount of re-captured stimulus agent.

Example 1. Collecting Gastrointestinal Samples with a Sampling Tube in Response to Dietary Stimulus Agent A device was constructed comprising a sampling tube made from silicone with a shore hardness of 50A measuring 2 meters long, 0.6 mm internal diameter and 1.2 mm outer diameter. The inlet portion of the sampling tube was a hole at the distal end of sampling tube 12 running through a silicone head element in the shape of an ellipsoid 8 mm in diameter and 18 mm long. The entire head element and the inlet portion of the sampling tube were wrapped in a nylon mesh with 150-micron pore size that served as the filtering element. The filtering element, when laid out as a flat sheet, had a surface area of 5 square centimeters.

The head element was swallowed and the distance traveled by the inlet portion of the sampling tube was recorded, along with the dietary stimulus agent and the gastrointestinal samples collected. Sampling was performed by pulling on a piston of a 3 ml syringe attached to the proximal end of the sampling tube which was taped to the cheek of the subject, thereby creating a vacuum in the sampling tube. Once full, the 3 ml syringe was replaced with a new syringe. Samples were collected directly into a series of 3 ml syringes that were the collection chambers. The dietary stimulus agents consisted of 50 grams of a liquid or blended ingredient wherein 50% or more the ingredient came from a single component from among the three groups of simple carbohydrates, fats and fiber. In addition, further stimulus agent of 500 mg acetaminophen as an active agent and 50 grams of a probiotic drink were also ingested. The time delay is the time between the ingestion of the stimulus agent until the sampling event, which gave the stimulus agent time to reach the GI tract region of interest. The distance measurement is the length of sampling tube from the mouth to the GI tract region of interest. When the distance reached 200 cm, the sampling tube was fixed outside the subject's mouth for the remaining 6.5 hours of sampling in order to limit the gastrointestinal samples to jejunal responses to multiple stimulus agents. At the end of the sampling procedure, the sampling tube was cut at the level of the mouth, swallowed and eliminated in the feces the next day. The subject reported no discomfort during the entire sampling procedure. Table 3 below shows the sampling and stimulus agent sequence for this experiment. The collected gastrointestinal samples were analyzed for their microbial DNA content and metabolomics profile using liquid chromatography/mass spectrometry techniques.

Figure 4:
FIG. 4 illustrates experimental results obtained from the present invention.
Figure 5:
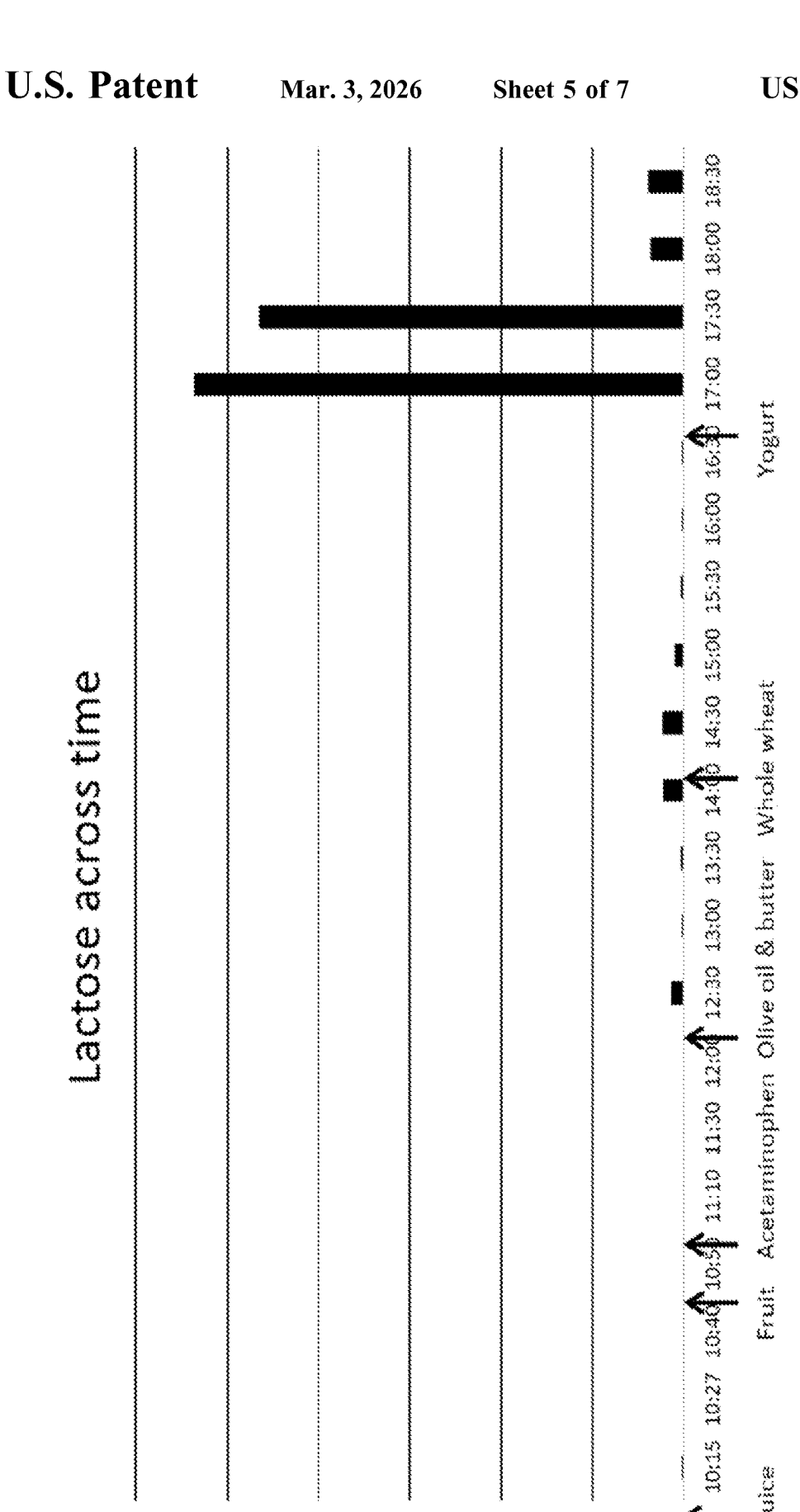
FIG. 5 illustrates experimental results obtained from the present invention.
Figure 6:
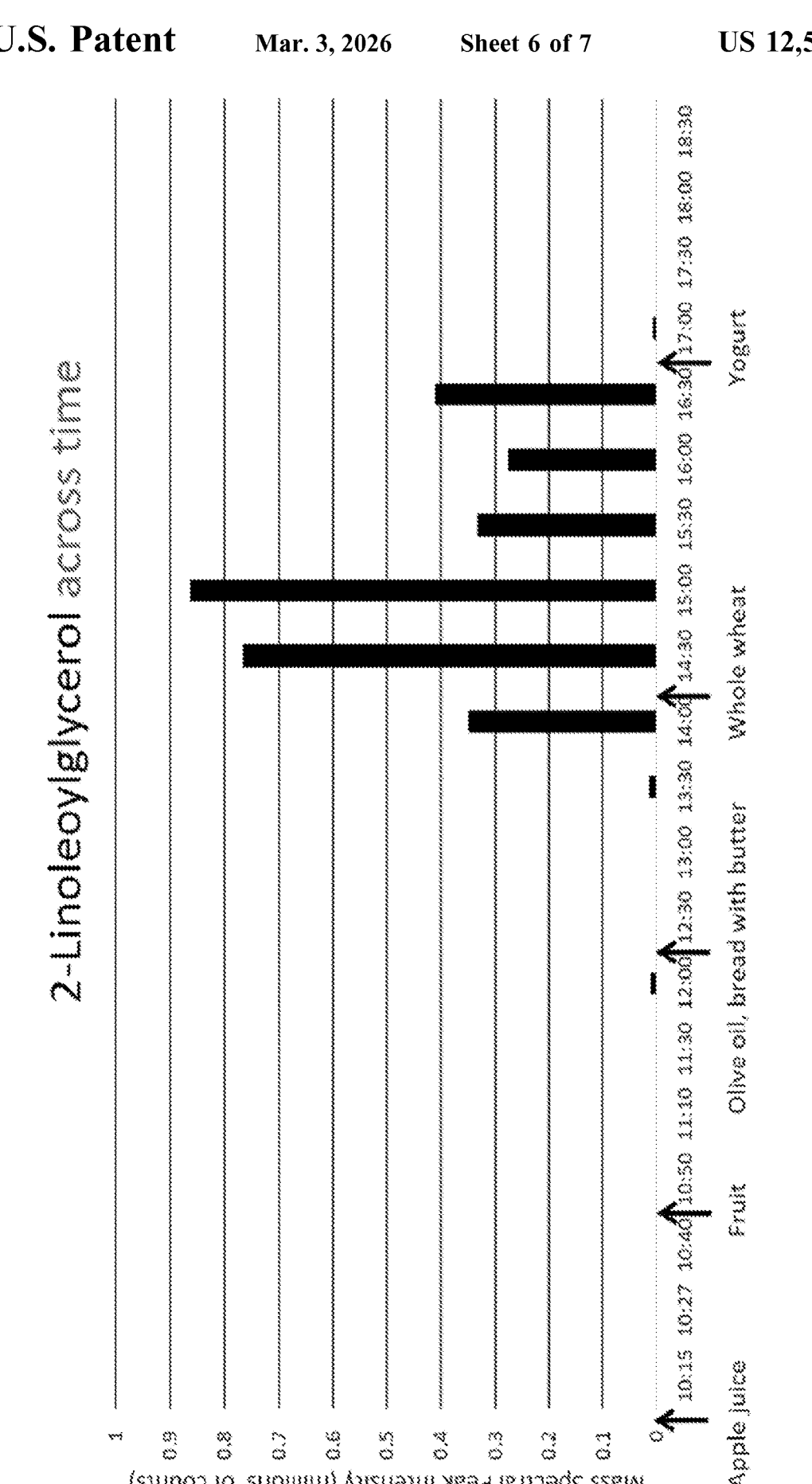
FIG. 6 illustrates experimental results obtained from the present invention.
Figure 7:
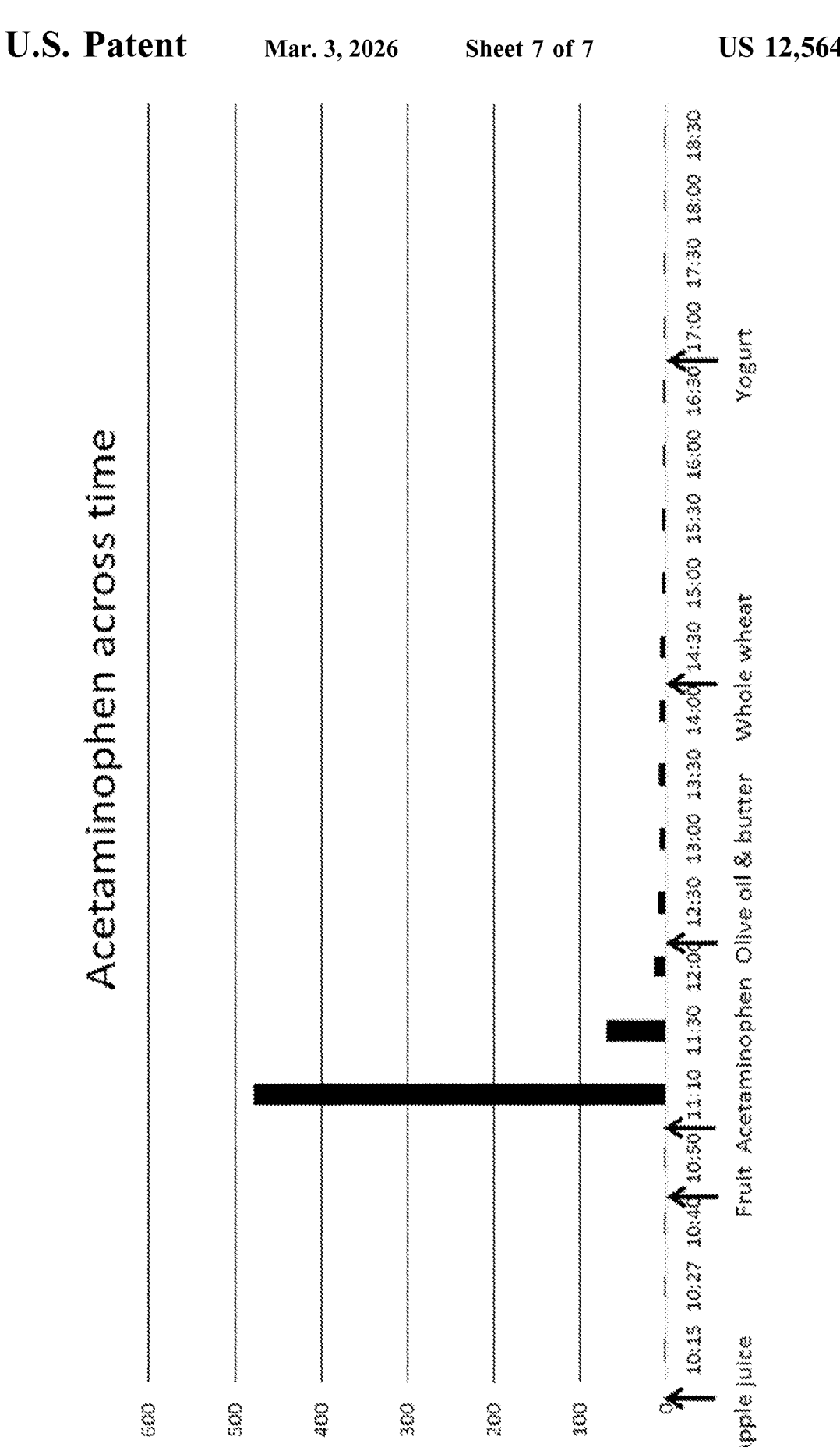
FIG. 7 illustrates experimental results obtained from the present invention.

FIGS. 4-7 shows the resulting liquid chromatography-mass spectrometry (LC-MS) metabolomics data from this sampling procedure with the relative amount of a metabolite along the Y-axis and time after ingestion of device 10 and the ingested dietary stimulus agents listed along the X-axis. FIG. 4 shows the profile of the bile acid glycocholic acid indicating cyclical release from the gallbladder after ingestion of food. FIG. 5 shows the profile of lactose peaking after ingestion of yogurt. FIG. 6 show shows the profile of 2-linoleylglycerol, which is a constituent of olives, peaking 2 hours after ingestion of olive oil. FIG. 7 shows the profile of acetaminophen peaking 30 minutes after ingestion of acetaminophen and exponentially decreasing thereafter.

TABLE 3

Timeline of a sequence of dietary stimulus agent coupled to a sampling sequence that measured the response of the GI tract to each stimulus agent in a sequential fashion.

| Sample | Time after ingestion (min) | Distance between inlet portion and mouth (cm) | pH | Inferred location | Stimulus agent | Time delay (min) | Gastrointestinal sample description |
|---|---|---|---|---|---|---|---|
| | 0 | | | | Water | | |
| 1 | 0:45 | | 1 | Stomach | | | Clear |
| 2 | 0:57 | | 1.6 | Stomach | | | Clear |
| 3 | 1:10 | 85 | 6.8 | Duodenum | | | Light green |
| | 1:15 | | | | Blended fruit | | |
| 4 | 1:20 | 105 | 6.6 | Duodenum | | 5 | Dark green |
| | 1:25 | | | | Acetaminophen | | |
| 5 | 1:40 | 145 | 5 | Jejunum | | 15 | Yellow |
| 6 | 2:00 | 160 | 6.1 | Jejunum | | 35 | Yellow |
| | 2:05 | | | | Blended fruit | | |
| 7 | 2:30 | 200 | 6.4 | Jejunum | | 25 | Yellow |
| | 2:40 | | | | Olive oil | | |
| 8 | 3:00 | 200 | 6.3 | Jejunum | | 20 | Green, oily |
| 9 | 3:30 | 200 | 6.7 | Jejunum | | 50 | Green, oily |
| 10 | 4:00 | 200 | 6.4 | Jejunum | | 80 | Dark green, oily |
| 11 | 4:30 | 200 | 6.3 | Jejunum | | 110 | Dark green |
| | 4:45 | | | | Whole wheat | | |
| 12 | 5:00 | 200 | 6.8 | Jejunum | | 15 | Dark green |
| 13 | 5:30 | 200 | 6.8 | Jejunum | | 45 | Dark green |
| 14 | 6:00 | 200 | 6.2 | Jejunum | | 75 | Dark green, oily |

TABLE 3-continued

Timeline of a sequence of dietary stimulus agent coupled to a sampling sequence that
measured the response of the GI tract to each stimulus agent in a sequential fashion.

| Sample | Time after ingestion (min) | Distance between inlet portion and mouth (cm) | pH | Inferred location | Stimulus agent | Time delay (min) | Gastrointestinal sample description |
|---|---|---|---|---|---|---|---|
| 15 | 6:30 | 200 | 6.4 | Jejunum | | 105 | Dark green, oily |
| 16 | 7:00 | 200 | 6.3 | Jejunum | | 135 | Dark green |
| | 7:05 | | | | Probiotics | | |
| 17 | 7:30 | 200 | 6.6 | Jejunum | | 25 | Yellow |
| 18 | 8:00 | 200 | 6.4 | Jejunum | | 55 | Yellow |
| 19 | 8:30 | 200 | 6.8 | Jejunum | | 85 | Whitish |
| 20 | 9:00 | 200 | 6.7 | Jejunum | | 115 | Yellow |

DNA was extracted and sequenced to a read depth of 3 million reads using metagenomic sequencing from three of the samples collected above, representing a distance of 105 cm, 160 cm and 200 cm between the lips and the inlet portion of the sampling tube. Based on a distance of 85 cm from the lips to the duodenum (see Table 3 above), the distances of sampling post-pylorus and intestinal regions sampled were 20 cm (duodenum), 75 cm (jejunum) and 115 cm (jejunum). Table 4 shows the identity of the microbial families detected in these distinct anatomical regions. Note the relative decrease of Micrococcaceae and Actinomycetaceae and the relative increase in Streptococcaceae and Veillonellaceae as the sampling device advanced in the intestinal tract. Strain level data was collected for each of these microbes as well, and the changing relative abundance indicates shifting microbial functions inside the small intestine as a function of longitudinal distance.

TABLE 4

The identity of the microbial families detected in three
distinct anatomical regions of the small intestine as collected
by the sampling device in a normal human subject.

| Microbial family | 105 cm Duodenum | 160 cm Jejunum | 200 cm Jejunum |
|---|---|---|---|
| Streptococcaceae | 34% | 44% | 44% |
| Micrococcaceae | 29% | 9% | 8% |
| Actinomycetaceae | 17% | 15% | 11% |
| Veillonellaceae | 5% | 8% | 16% |
| Lachnospiraceae | 4% | 7% | 5% |
| Flavobacteriaceae | 3% | 6% | 2% |
| Bacillales | 2% | 4% | 7% |
| Peptoniphilaceae | 2% | 1% | 1% |
| Atopobiaceae | 1% | 1% | 1% |
| Clostridiales | 1% | 1% | 1% |
| Prevotellaceae | 1% | 1% | 0% |
| Neisseriaceae | 1% | 1% | 3% |
| Carnobacteriaceae | 1% | 2% | 1% |

The above example demonstrates that the device of the present invention is capable of collecting gastrointestinal samples from regions of interest in the GI tract while single-component ingested stimulus agents are used to assess the functional responses of the GI tract. Furthermore, gut microbial identities can be identified in distinct intestinal regions.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

I claim:

1. A device for collecting gastrointestinal samples comprising a swallowable head element enclosing a wound portion of a sampling tube having a distal end with an inlet portion positioned through said head element and a proximal end in fluid communication with a collection chamber, wherein said collection chamber is positionable outside a subject's mouth and gastrointestinal tract when said inlet portion of said sampling tube is within the gastrointestinal tract of said subject.

2. The device of claim 1, wherein said sampling tube exits or unwinds from said head element as said head element is swallowed.

3. The device of claim 1, wherein said head element is non-degradable.

4. The device of claim 1, wherein a vacuum is applied to said collection chamber to pull gastrointestinal samples into said collection chamber through inlet portion at said distal end of said sampling tube.

5. The device of claim 1, wherein said collection chamber is a reservoir tube in which the collected gastrointestinal samples are stored as discrete samples arranged in a linear array.

6. The device of claim 5, wherein said linear array of said gastrointestinal samples stored in said reservoir tube is a recapitulation of the linear order of the fluids collected from the GI tract.

7. The device of claim 5, wherein said reservoir tube is an extension of said sampling tube.

8. The device of claim 7, wherein an inner diameter of said reservoir tube is greater than an inner diameter of said sampling tube.

9. The device in claim 1, wherein said gastrointestinal samples arriving through said sampling tube are diverted into discrete collection chambers, thereby separating the collected GI fluids in discrete sample containers.

10. The device in claim 1, wherein said collection chamber is evacuated and the rupture of a membrane or septum covering said evacuated chamber drives the vacuum-driven flow of gastrointestinal fluids through said sampling tube into said collection chamber.

11. The device of claim 1, wherein the flow of said gastrointestinal samples into said sampling tube is reversed when lack of adequate forward flow of said gastrointestinal samples inside said sampling tube is detected by a flow sensor.

12. The device of claim 1, wherein said head element comprises a pump that forces GI fluids through said sampling tube and outside the subject's mouth and gastrointestinal tract using positive pressure or direct displacement.

13. The device of claim 1, wherein the device releases an agent into the gastrointestinal tract.

14. The device of claim 1, wherein said sampling tube comprises shorter sections that are connected with linker elements that mechanically degrade in moisture over a preset time period.

15. The device of claim 1, wherein a connection between said sampling tube and said head element mechanically degrades after being present in the gastrointestinal tract for a predetermined time range.

\* \* \* \* \*